United States Patent
Reddy et al.

(10) Patent No.: US 6,646,009 B2
(45) Date of Patent: Nov. 11, 2003

(54) N-(ARYL)-2-ARYLETHENESULFONAMIDES AND THERAPEUTIC USES THEREOF

(75) Inventors: E. Premkumar Reddy, Villanova, PA (US); M.V. Ramana Reddy, Upper Darby, PA (US); Stanley C. Bell, Narberth, PA (US)

(73) Assignees: Temple University — Of Commonwealth System of Higher Education, Philadelphia, PA (US); Onconova Therapeutics, Inc., Lawrenceville, NJ (US)

( * ) Notice: Subject to any disclaimer, the term of this patent is extended or adjusted under 35 U.S.C. 154(b) by 0 days.

(21) Appl. No.: 10/085,826

(22) Filed: Feb. 28, 2002

(65) Prior Publication Data

US 2002/0165412 A1 Nov. 7, 2002

Related U.S. Application Data

(60) Provisional application No. 60/271,985, filed on Feb. 28, 2001.

(51) Int. Cl.[7] ......... A61K 31/18; A61K 31/47; A61K 31/425; A61K 31/42; A61K 31/415
(52) U.S. Cl. ......... 514/604; 514/314; 514/357; 514/367; 514/375; 514/400; 514/359; 514/427; 546/172; 546/331; 548/179; 548/217; 548/267.2; 548/323.5; 548/561; 564/82; 564/91; 564/92
(58) Field of Search .......... 514/604, 314, 514/367, 375, 400, 359, 427, 357; 564/89, 82, 91, 92; 546/172, 331; 548/179, 217, 267.2, 323.5, 561

(56) References Cited

U.S. PATENT DOCUMENTS

| | | | |
|---|---|---|---|
| 4,035,421 A | 7/1977 | Snyder, Jr. | 260/556 |
| 5,302,724 A | 4/1994 | Howbert et al. | 548/452 |
| 5,880,151 A | 3/1999 | Medina et al. | 514/518 |
| 5,886,044 A | 3/1999 | Widdowson et al. | 514/596 |
| 6,121,304 A | 9/2000 | Flygare et al. | 514/403 |
| 6,191,170 B1 * | 2/2001 | Medina | 514/604 |

FOREIGN PATENT DOCUMENTS

| | | |
|---|---|---|
| DE | 2118493 | 10/1972 |
| WO | WO 00/17159 | 3/2000 |

OTHER PUBLICATIONS

CA:78:15764m, abstracting Ger. Offen. 2,118,493 (Oct. 26, 1972).
Waldau and Putter, Agnew. Chem., Int., Ed. Engl. 11(9), 826–8 (1972).
J.E. Oliver and A.B. DeMilo, Synthesis, 321–322 (1975).
B. Aswarthamma, et al., Chimica Acta Turcica 24 (1996), pp. 7–10.
A. Touati, et al. J.Soc.Alger.Chim., 1996, 6(1), pp. 39–52.
P. Wipf, et al., Bioorganic & Medicinal Chemistry Letters 11 (2001) pp. 313–317.

* cited by examiner

Primary Examiner—Peter O'Sullivan
(74) Attorney, Agent, or Firm—Drinker Biddle & Reath LLP

(57) ABSTRACT

N-(Aryl)-2-arylethenesulfonamides and pharmaceutically acceptable salts and compositions thereof are useful as antiproliferative agents, including, for example, anticancer agents. They are also useful as radioprotective agents.

79 Claims, 2 Drawing Sheets

N-(ARYL)-2-ARYLETHENESULFONAMIDES AND THERAPEUTIC USES THEREOF

CROSS-REFERENCE TO RELATED APPLICATION

This application claims the priority of copending U.S. Provisional Application Ser. No. 60/271,985 filed Feb. 28, 2001, the entire disclosure of which is herein incorporated by reference.

FIELD OF THE INVENTION

The invention relates to compositions and methods for the treatment of proliferative disorders, including but not limited to cancer. The invention relates to the field of protecting normal cells and tissues from anticipated, planned or inadvertent exposure to ionizing radiation.

BACKGROUND OF THE INVENTION

α-β-Unsaturated Sulfonamides

Cancer remains a leading cause of mortality in the United States and in the world. To be useful, a new chemotherapeutic agent should have a wide spectrum of activity and significant therapeutic index. Styrene-ω-sulfonanilide has been prepared by reacting styrylsulfonyl chloride with aniline (Bordwell et al., *J. Amer. Chem. Soc.* 68:139, 1946). This and certain other styrene-ω-sulfonanilides have been prepared by Knoevenagel-type synthesis as possible chemosterilants against the common house fly *Musca domestica* L. (Oliver et al, *Synthesis* 321–322, 1975).

U.S. Pat. No. 4,035,421 to Snyder, Jr. describes the preparation of N-(3,4-dichlorophenyl)-2-phenylethenesulfonamide and its use as an antibacterial agent.

The styrene-ω-sulfonanilides 3'-hydroxy-4-nitrostyrene-β-sulfonanilide, 3'-hydroxy-2-nitrostyrene-β-sulfonanilide and 5'-hydroxy-2'-methyl-4-nitrostyrene-β-sulfonanilide were utilized as intermediates in the preparation of certain stilbenes by Waldau et al. *Angew. Chem., Int. Ed. Engl.* 11(9):826–818 (1972). The styrene-ω-sulfonanilides 3'-hydroxy-3-nitrostyrene-β-sulfonanilide and 5'-hydroxy-2'-methyl-4-nitrostyrene-β-sulfonanilide have been utilized in the preparation of stilbenes used as dyes (DE 2118493—Farbenfab AG).

Aswarthamma et al., *Chimica Acta Turcica* 24:7–10 (1996) disclose the preparation of certain trans-(1-aryl-(2-anilinesulphonyl)ethylenes. No biological activity is set forth for the compounds. Touarti et al., *J. Soc. Alger. Chim.* 6(1):39–52 (1996) disclose the preparation of certain α,β-unsaturated sulfonamides for inhibition of coniferyl alcohol dehydrogenase (CADH).

Except for the isolated teaching of antibacterial activity of N-(3,4-dichlorophenyl)-2-phenylethenesulfonamide, no useful pharmaceutical activity has been proposed for the limited numbers of α,β-unsaturated sulfonamides known to the prior art. In particular, no anti-cell proliferation or anticancer utility has been proposed for this class of compounds.

New cell antiproliferative agents, and anticancer therapeutics in particular, are needed which are useful in inhibiting proliferation of and/or killing cancer cells. In particular, such agents are needed which are selective in the killing of proliferating cells such as tumor cells, but not normal cells. Antineoplasitc agents are needed which are effective against a broad range of tumor types.

Ionizing Radiation Health Risks

Ionizing radiation has an adverse effect on cells and tissues, primarily through cytotoxic effects. In humans, exposure to ionizing radiation occurs primarily through therapeutic techniques (such as anticancer radiotherapy) or through occupational and environmental exposure.

A major source of exposure to ionizing radiation is the administration of therapeutic radiation in the treatment of cancer or other proliferative disorders. Depending on the course of treatment prescribed by the treating physician, multiple doses may be received by a subject over the course of several weeks to several months.

Therapeutic radiation is generally applied to a defined area of the subject's body which contains abnormal proliferative tissue, in order to maximize the dose absorbed by the abnormal tissue and minimize the dose absorbed by the nearby normal tissue. However, it is difficult (if not impossible) to selectively administer therapeutic ionizing radiation to the abnormal tissue. Thus, normal tissue proximate to the abnormal tissue is also exposed to potentially damaging doses of ionizing radiation throughout the course of treatment. There are also some treatments that require exposure of the subject's entire body to the radiation, in a procedure called "total body irradiation", or "TBI." The efficacy of radiotherapeutic techniques in destroying abnormal proliferative cells is therefore balanced by associated cytotoxic effects on nearby normal cells. Because of this, radiotherapy techniques have an inherently narrow therapeutic index which results in the inadequate treatment of most tumors. Even the best radiotherapeutic techniques may result in incomplete tumor reduction, tumor recurrence, increasing tumor burden, and induction of radiation resistant tumors.

Numerous methods have been designed to reduce normal tissue damage while still delivering effective therapeutic doses of ionizing radiation. These techniques include brachytherapy, fractionated and hyperfractionated dosing, complicated dose scheduling and delivery systems, and high voltage therapy with a linear accelerator. However, such techniques only attempt to strike a balance between the therapeutic and undesirable effects of the radiation, and full efficacy has not been achieved.

For example, one treatment for subjects with metastatic tumors involves harvesting their hematopoietic stem cells and then treating the subject with high doses of ionizing radiation. This treatment is designed to destroy the subject's tumor cells, but has the side effect of also destroying their normal hematopoietic cells. Thus, a portion of the subject's bone marrow (containing the hematopoietic stem cells), is removed prior to radiation therapy. Once the subject has been treated, the autologous hematopoietic stem cells are returned to their body.

However, if tumor cells have metastasized away from the tumor's primary site, there is a high probability that some tumor cells will contaminate the harvested hematopoietic cell population. The harvested hematopoietic cell population may also contain neoplastic cells if the subject suffers from a cancers of the bone marrow such as the various French-American-British (FAB) subtypes of acute myelogenous leukemias (AML), chronic myeloid leukemia (CML), or acute lymphocytic leukemia (ALL). Thus, the metastasized tumor cells or resident neoplastic cells must be removed or killed prior to reintroducing the stem cells to the subject. If any living tumorigenic or neoplastic cells are reintroduced into the subject, they can lead to a relapse.

Prior art methods of removing tumorigenic or neoplastic cells from harvested bone marrow are based on a whole-population tumor cell separation or killing strategy, which typically does not kill or remove all of the contaminating malignant cells. Such methods include leukopheresis of mobilized peripheral blood cells, immunoaffinity-based selection or killing of tumor cells, or the use of cytotoxic or photosensitizing agents to selectively kill tumor cells. In the best case, the malignant cell burden may still be at 1 to 10 tumor cells for every 100,000 cells present in the initial harvest (Lazarus et al. J. of Hematotherapy, 2(4):457–66, 1993).

Thus, there is needed a purging method designed to selectively destroy the malignant cells present in the bone marrow, while preserving the normal hematopoietic stem cells needed for hematopoietic reconstitution in the transplantation subject.

Exposure to ionizing radiation can also occur in the occupational setting. Occupational doses of ionizing radiation may be received by persons whose job involves exposure (or potential exposure) to radiation, for example in the nuclear power and nuclear weapons industries. Military personnel stationed on vessels powered by nuclear reactors, or soldiers required to operate in areas contaminated by radioactive fallout, risk similar exposure to ionizing radiation. Occupational exposure may also occur in rescue and emergency personnel called in to deal with catastrophic events involving a nuclear reactor or radioactive material. Other sources of occupational exposure may be from machine parts, plastics, and solvents left over from the manufacture of radioactive medical products, smoke alarms, emergency signs, and other consumer goods. Occupational exposure may also occur in persons who serve on nuclear powered vessels, particularly those who tend the nuclear reactors, in military personnel operating in areas contaminated by nuclear weapons fallout, and in emergency personnel who deal with nuclear accidents. Environmental exposure to ionizing radiation may also result from nuclear weapons detonations (either experimental or during wartime), discharges of actinides from nuclear waste storage and processing and reprocessing of nuclear fuel, and from naturally occurring radioactive materials such as radon gas or uranium. There is also increasing concern that the use of ordnance containing depleted uranium results in low-level radioactive contamination of combat areas.

Radiation exposure from any source can be classified as acute (a single large exposure) or chronic (a series of small low-level, or continuous low-level exposures spread over time). Radiation sickness generally results from an acute exposure of a sufficient dose, and presents with a characteristic set of symptoms that appear in an orderly fashion, including hair loss, weakness, vomiting, diarrhea, skin burns and bleeding from the gastrointestinal tract and mucous membranes. Genetic defects, sterility and cancers (particularly bone marrow cancer) often develop over time. Chronic exposure is usually associated with delayed medical problems such as cancer and premature aging. An acute a total body exposure of 125,000 millirem may cause radiation sickness. Localized doses such as are used in radiotherapy may not cause radiation sickness, but may result in the damage or death of exposed normal cells.

For example, an acute total body radiation dose of 100,000–125,000 millirem (equivalent to 1 Gy) received in less than one week would result in observable physiologic effects such as skin burns or rashes, mucosal and GI bleeding, nausea, diarrhea and/or excessive fatigue. Longer term cytotoxic and genetic effects such as hematopoietic and immunocompetent cell destruction, hair loss (alopecia), gastrointestinal, and oral mucosal sloughing, venoocclusive disease of the liver and chronic vascular hyperplasia of cerebral vessels, cataracts, pneumonites, skin changes, and an increased incidence of cancer may also manifest over time. Acute doses of less than 10,000 millirem (equivalent to 0.1 Gy) typically will not result in immediately observable biologic or physiologic effects, although long term cytotoxic or genetic effects may occur.

A sufficiently large acute dose of ionizing radiation, for example 500,000 to over 1 million millirem (equivalent to 5–10 Gy), may kill a subject immediately. Doses in the hundreds of thousands of millirems may kill within 7 to 21 days from a condition called "acute radiation poisoning." Reportedly, some of the Chernobyl firefighters died of acute radiation poisoning, having received acute doses in the range of 200,000–600,000 millirem (equivalent to 2–6 Gy). Acute doses below approximately 200,000 millirem do not result in death, but the exposed subject will likely suffer long-term cytotoxic or genetic effects as discussed above.

Acute occupational exposures usually occur in nuclear power plant workers exposed to accidental releases of radiation, or in fire and rescue personnel who respond to catastrophic events involving nuclear reactors or other sources of radioactive material. Suggested limits for acute occupational exposures in emergency situations were developed by the Brookhaven National Laboratories, and are given in Table 1.

TABLE 1

Acute Occupational Exposure Limits for Emergency Operations

| Whole Body Conditions for Dose Limit | Activity Required | Conditions for Exposure |
| --- | --- | --- |
| 10,000 millirem* | Protect property | Voluntary, when lower dose not practical |
| 25,000 millirem | Lifesaving Operation; Protect General Public | Voluntary, when lower dose not practical |
| >25,000 millirem | Lifesaving operation; Protect large population | Voluntary, when lower dose not practical, and the risk has been clearly explained |

*100,000 millirem equals one sievert (Sv). For penetrating radiation such as gamma radiation, one Sv equals approximately one Gray (Gy). Thus, the dosage in Gy can be estimated as 1 Gy for every 100,000 millirem.

A chronic dose is a low level (i.e., 100–5000 millirem) incremental or continuous radiation dose received over time. Examples of chronic doses include a whole body dose of ~5000 millirem per year, which is the dose typically received by an adult working at a nuclear power plant. By contrast, the Atomic Energy Commission recommends that members of the general public should not receive more than 100 millirem per year. Chronic doses may cause long-term cytotoxic and genetic effects, for example manifesting as an increased risk of a radiation-induced cancer developing later in life. Recommended limits for chronic exposure to ionizing radiation are given in Table 2.

TABLE 2

Annual Chronic Occupational Radiation Exposure Limits

| Organ or Subject | Annual Occupational Dose in millirem |
| --- | --- |
| Whole Body | 5000 |
| Lens of the Eye | 15,000 |
| Hands and wrists | 50,000 |
| Any individual organ | 50,000 |
| Pregnant worker | 500/9 months |
| Minor (16–18) receiving training | 100 |

By way of comparison, Table 3 sets forth the radiation doses from common sources.

TABLE 3

Radiation Dosages From Common Sources

| Sources | Dose In Millirem |
| --- | --- |
| Television | <1/yr |
| Gamma Rays, Jet Cross Country | 1 |
| Mountain Vacation - 2 week | 3 |
| Atomic Test Fallout | 5 |
| U.S. Water, Food & Air (Average) | 30/yr |
| Wood | 50/yr |
| Concrete | 50/yr |
| Brick | 75/yr |
| Chest X-Ray | 100 |
| Cosmic Radiation (Sea Level) | 40/yr (add 1 millirem/ 100 ft elev.) |
| Natural Background San Francisco | 120/yr |
| Natural Background Denver | 50/yr |
| Atomic Energy Commission Limit For Workers | 5000/yr |
| Complete Dental X-Ray | 5000 |
| Natural Background at Pocos de Caldras, Brazil | 7000/yr |
| Whole Body Diagnostic X-Ray | 100,000 |
| Cancer Therapy | 500,000 (localized) |
| Radiation Sickness-Nagasaki | 125,000 (single doses) |
| $LD_{50}$ Nagasaki & Hiroshima | 400,000–500,000 (single dose) |

Chronic doses of greater than 5000 millirem per year (0.05 Gy per year) may result in long-term cytotoxic or genetic effects similar to those described for persons receiving acute doses. Some adverse cytotoxic or genetic effects may also occur at chronic doses of significantly less than 5000 millirem per year. For radiation protection purposes, it is assumed that any dose above zero can increase the risk of radiation-induced cancer (i.e., that there is no threshold). Epidemiologic studies have found that the estimated lifetime risk of dying from cancer is greater by about 0.04% per rem of radiation dose to the whole body.

While anti-radiation suits or other protective gear may be effective at reducing radiation exposure, such gear is expensive, unwieldy, and generally not available to public. Moreover, radioprotective gear will not protect normal tissue adjacent a tumor from stray radiation exposure during radiotherapy. What is needed, therefore, is a practical way to protect subjects who are scheduled to incur, or are at risk for incurring, exposure to ionizing radiation. In the context of therapeutic irradiation, it is desirable to enhance protection of normal cells while causing tumor cells to remain vulnerable to the detrimental effects of the radiation. Furthermore, it is desirable to provide systemic protection from anticipated or inadvertent total body irradiation, such as may occur with occupational or environmental exposures, or with certain therapeutic techniques.

Pharmaceutical radioprotectants offer a cost-efficient, effective and easily available alternative to radioprotective gear. However, previous attempts at radioprotection of normal cells with pharmaceutical compositions have not been entirely successful. For example, cytokines directed at mobilizing the peripheral blood progenitor cells confer a myeloprotective effect when given prior to radiation (Neta et al., Semin. Radiat. Oncol. 6:306–320, 1996), but do not confer systemic protection. Other chemical radioprotectors administered alone or in combination with biologic response modifiers have shown minor protective effects in mice, but application of these compounds to large mammals was less successful, and it was questioned whether chemical radioprotection was of any value (Maisin, J. R., Bacq and Alexander Award Lecture. "Chemical radioprotection: past, present, and future prospects", Int J. Radiat Biol. 73:443–50, 1998). Pharmaceutical radiation sensitizers, which are known to preferentially enhance the effects of radiation in cancerous tissues, are clearly unsuited for the general systemic protection of normal tissues from exposure to ionizing radiation.

What is needed are therapeutic agents to protect subjects who have incurred, or are at risk for incurring exposure to ionizing radiation. In the context of therapeutic irradiation, it is desirable to enhance protection of normal cells while causing tumor cells to remain vulnerable to the detrimental effects of the radiation. Furthermore, it is desirable to provide systemic protection from anticipated or inadvertent total body irradiation, such as may occur with occupational or environmental exposures, or with certain therapeutic techniques.

SUMMARY OF THE INVENTION

It is an object of the invention to provide compounds, compositions and therapeutic methods. The biologically active compounds are in the form of N-(aryl)-2-arylethenesulfonamides, and pharmaceutically acceptable salts thereof.

It is an object of the invention to provide compounds, compositions and methods for the treatment of cancer and other proliferative diseases.

It is an object of the invention to provide compounds which are selective in killing tumor cells but not normal cells.

It is an object of the invention to provide compounds, compositions and methods for inducing neoplastic cells to selectively undergo apoptosis.

It is an object of the invention to provide compounds, compositions and methods for protecting normal cells and tissues from the cytotoxic and genetic effects of exposure to ionizing radiation, in subjects who have incurred or are at risk for incurring exposure to ionizing radiation. The exposure to ionizing radiation may occur in controlled doses during the treatment of cancer and other proliferative disorders, or may occur in uncontrolled doses beyond the norm accepted for the population at large during high risk activities or environmental exposures.

In another aspect, a method of treating a subject for cancer or other proliferative disorders is provided, comprising administering to the subject an effective amount of at least one radioprotectant N-(aryl)-2-arylethenesulfonamide compound prior to administering an effective amount of ionizing radiation, wherein the radioprotective N-(aryl)-2-arylethenesulfonamide compound induces a temporary radioresistant phenotype in the subject's normal tissue.

In a further aspect, the invention provides a method of safely increasing the dosage of therapeutic ionizing radiation used in the treatment of cancer or other proliferative disorders, comprising administering an effective amount of at least one radioprotective N-(aryl)-2-arylethenesulfonamide compound prior to administration of the therapeutic ionizing radiation, which radioprotective compound induces a temporary radioresistant phenotype in the subject's normal tissue.

In yet a further aspect, the invention provides a method for treating individuals who have incurred or are at risk for incurring remediable radiation damage from exposure to ionizing radiation. In one embodiment, an effective amount of at least one radioprotective N-(aryl)-2-arylethenesulfonamide compound is administered to the subject before the subject incurs remediable radiation damage from exposure to ionizing radiation. In another embodiment, an effective amount of at least one radioprotective N-(aryl)-2-arylethenesulfonamide compound is administered to the subject after the subject incurs remediable radiation damage from exposure to ionizing radiation.

In yet another embodiment, the invention provides a method for purging bone marrow of neoplastic cells (such as leukemic cells) or tumor cells which have metastasized into the bone marrow, comprising harvesting bone marrow cells from an individual afflicted with a proliferative disorder, treating the harvested bone marrow cells with an effective amount of at least one N-(aryl)-2-arylethenesulfonamide compound, and subjecting the treated bone marrow cells to an effective amount of ionizing radiation. The harvested cells are then returned to the body of the afflicted individual.

In another aspect, the invention is directed to novel compounds of formula I:

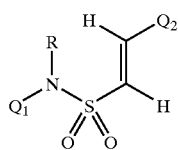

wherein:
  $Q_1$, and $Q_2$ are independently selected from the group consisting of substituted and unsubstituted aryl, and substituted and unsubstituted heteroaryl;
  R is selected from the group consisting of hydrogen, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$hydroxyalkyl, substituted aryl, unsubstituted aryl, substituted heteroaryl, unsubstituted heteroaryl, substituted aryl$(C_1-C_3)$alkyl, unsubstituted aryl$(C_1-C_3)$alkyl, substituted heteroaryl$(C_1-C_3)$alkyl and unsubstituted heteroaryl$(C_1-C_3)$alkyl;
  wherein the substituents for the substituted aryl and substituted heteroaryl groups comprising $Q_1$ are independently selected from the group consisting of halogen, C1–C6 alkyl, C1–C6 alkoxy, nitro, cyano, carboxy, carboxy(C1–C3)alkoxy, hydroxy, (C2–C6) hydroxyalkyl, phosphonato, amino, (C1–C6) acylamino, sulfamyl, acetoxy, di(C1–C6)alkylamino (C2–C6 alkoxy), trifluoromethyl and
  wherein the substituents for the substituted aryl and substituted heteroaryl groups comprising $Q_1$, are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$acylamino, sulfamyl, acetoxy, di$(C_1-C_6)$alkylamino$(C_2-C_6)$alkoxy, trifluoromethyl and

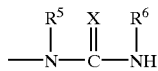

wherein:
  X is oxygen or sulfur,
  $R^5$ is selected from the group consisting of hydrogen, $(C_1-C_6)$alkyl, $(C_2-C_6)$heteroalkyl, substituted phenyl and unsubstituted phenyl, and
  $R^6$ is selected from the group consisting of hydrogen, $(C_1-C_6)$alkyl, $(C_2-C_6)$heteroalkyl, substituted aryl, unsubstituted aryl, substituted heteroaryl, unsubstituted heteroaryl, substituted aryl-$(C_1-C_3)$alkyl, unsubstituted aryl-$(C_1-C_3)$alkyl and $(C_1-C_6)$ alkoxycarbonyl$(C_1-C_6)$alkylenyl; and
wherein the substituents for the substituted aryl and substituted heteroaryl groups comprising $Q_2$, and the substituents for the substituted aryl and substituted heteroaryl groups comprising or included within R, $R^5$ and $R^6$, are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$ acylamino, sulfamyl, acetoxy, di$(C_1-C_6)$alkylamino $(C_2-C_6)$alkoxy and trifluoromethyl;
provided, that when R is hydrogen:
  (a) when $Q_1$ is unsubstituted phenyl, $Q_2$ is other than dimethoxyphenyl, 2-methylphenyl, 2-chlorophenyl, 4-chlorophenyl, 4-N,N-dimethylaminophenyl, 4-methylphenyl, 4-methoxyphenyl, 4-nitrophenyl, 3-methoxy-4-hydroxyphenyl, unsubstituted phenyl, unsubstituted phenyl, unsubstituted benzodioxolyl, unsubstituted 1-naphthyl and unsubstituted 2-thienyl; in a sub-embodiment, when $Q_1$ is unsubstituted phenyl, $Q_2$ is other than dialkoxyphenyl, 2-alkylphenyl, 2-halophenyl, 4-halophenyl, 4-N,N-dialkylaminophenyl, 4-alkylphenyl, 4-alkoxyphenyl, 4-nitrophenyl, 3-alkoxy-4-hydroxyphenyl, unsubstituted phenyl, unsubstituted phenyl, unsubstituted benzodioxolyl, unsubstituted 1-naphthyl and unsubstituted 2-thienyl;
  (b) when $Q_1$ is 2,4-dinitrophenyl, $Q_2$ is other than 4-methylphenyl, 4-methoxyphenyl, 4-nitrophenyl, 4-bromophenyl, 3,4-dichlorophenyl, unsubstituted phenyl or unsubstituted 1-naphthyl; in a sub-embodiment, when $Q_1$ is 2,4-dinitrophenyl, $Q_2$ is other than 4-alkylphenyl, 4-alkoxyphenyl, 4-nitrophenyl, 4-halophenyl, 3,4-dihalophenyl, unsubstituted phenyl or unsubstituted 1-naphthyl;
  (c) when $Q_1$ is 3-hydroxyphenyl, $Q_2$ is other than 2-nitrophenyl, or 3-nitrophenyl; in a sub-embodiment, when $Q_1$ is 3-hydroxyphenyl, $Q_2$ is other than nitrophenyl;
  (d) when $Q_1$ is 2-methyl-5-hydroxyphenyl, $Q_2$ is other than 4-nitrophenyl; in a sub-embodiment, when $Q_1$ is 2-methyl-5-hydroxyphenyl, $Q_2$ is other than 4-nitrophenyl;
  (e) when $Q_1$ is unsubstituted 2-pyridyl, $Q_2$ is other than 3-methoxy-4-hydroxyphenyl; in a sub-embodiment, when $Q_1$ is unsubstituted 2-pyridyl, $Q_2$ is other than 3-methoxy-4-hydroxyphenyl; and
  (f) when $Q_2$ is unsubstituted phenyl, $Q_1$ is other than 2-hydroxyphenyl, 2-aminophenyl, 3,4-dichlorophenyl or unsubstituted 2-pyridyl; in a sub-embodiment, when $Q_2$ is unsubstituted phenyl, $Q_1$ is other than 2-hydroxyphenyl, 2-aminophenyl, 3,4-dihalophenyl or unsubstituted 2-pyridyl; or a pharmaceutically acceptable salt thereof.

In a further sub-embodiment, novel compounds of formula I are provided wherein $Q_1$ and $Q_2$ are independently selected from the group consisting of substituted aryl and substituted heteroaryl; R is defined as above; the substituents for the substituted aryl and substituted heteroaryl groups comprising $Q_1$ are defined as above; the substituents for the substituted aryl and substituted heteroaryl groups comprising $Q_2$, and the substituents for the substituted aryl and substituted heteroaryl groups comprising or included within R, $R^5$ and $R^6$, are defined as above, provided, when R is hydrogen:
(i) $Q_1$ may not be dinitrophenyl;
(ii) $Q_2$ may not be dinitrophenyl; and
(iii) when $Q_2$ is mononitrophenyl:
   $Q_1$ is other than substituted phenyl, or
   $Q_1$ is substituted phenyl wherein at least the 4-position is substituted, and the substituent is other than hydroxy;

or a pharmaceutically acceptable salt thereof.

According to another embodiment, the invention is directed to a process for preparing a novel compound as defined above, the process comprising reacting a compound of the formula B:

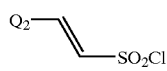

B with a compound of the formula C

C in a nonprotic solvent in the presence of a base to form a compound of the formula:

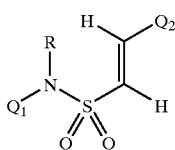

I wherein R, $Q_1$ and $Q_2$ are defined as above. Compound B may be prepared by reacting a compound of the formula A, $Q_2$—CH=CH$_2$, with sulfonyl chloride in the presence of a nonprotic solvent.

According to another embodiment, the invention is directed to an alternative process for preparing a novel compound as defined above, said process comprising reacting a compound of the formula G

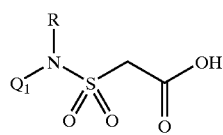

G with a compound of the formula H

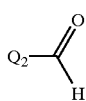

H in the presence of a basic catalyst to form a compound of the formula:

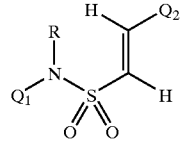

I wherein R, $Q_1$ and $Q_2$ are defined as above.

Compounds of formula G may be prepared by reacting a compound of the formula E, ClSO$_2$—CH$_2$—C(O)OR', with a compound of formula C (as defined above) in a nonprotic solvent in the presence of a base to form a compound of the formula F,

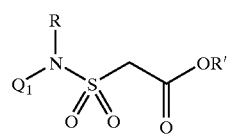

F and then treating the formula F compound with a base capable of hydrolyzing the ester function thereof to an acid to form compound G; wherein R and $Q_1$ are defined as above, and R' is methyl or ethyl.

According to another embodiment of the invention, pharmaceutical compositions are provided comprising a pharmaceutically acceptable carrier and a compound according to formula I wherein
   $Q_1$ and $Q_2$ are independently selected from the group consisting of substituted and unsubstituted aryl, and substituted and unsubstituted heteroaryl; and R is defined as above;
   wherein the substituents for the substituted aryl and substituted heteroaryl groups comprising $Q_1$ are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$acylamino, sulfamyl, acetoxy, di$(C_1-C_6)$alkylamino$(C_2-C_6)$alkoxy, trifluoromethyl and

wherein:
X is oxygen or sulfur,
$R^5$ is selected from the group consisting of hydrogen, $(C_1-C_6)$alkyl, $(C_2-C_6)$heteroalkyl, substituted phenyl and unsubstituted phenyl, and
$R^6$ is selected from the group consisting of hydrogen, $(C_1-C_6)$alkyl, $(C_2-C_6)$heteroalkyl, substituted aryl, unsubstituted aryl, substituted heteroaryl, unsubstituted heteroaryl, substituted aryl-$(C_1-C_3)$alkyl, unsubstituted aryl-$(C_1-C_3)$alkyl and $(C_1-C_6)$alkoxycarbonyl$(C_1-C_6)$alkylenyl; and
wherein the substituents for the substituted aryl and substituted heteroaryl groups comprising $Q_2$, and the substituents for the substituted aryl and substituted heteroaryl groups comprising or included within R, $R^5$ and $R^6$, are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$acylamino, sulfamyl, acetoxy, di$(C_1-C_6)$alkylamino$(C_2-C_6)$alkoxy and trifluoromethyl;

provided, when R is hydrogen and $Q_2$ is unsubstituted phenyl, then $Q_1$ must be other than 3,4-dichlorophenyl, more particularly other than 3,4-dihalophenyl, even more particularly other than dihalophenyl;

or a pharmaceutically acceptable salt thereof.

According to another embodiment of the invention, a method of treating an individual for a proliferative disorder comprises administering to said individual an effective amount of at least one N-(aryl)-2-arylethenesulfonamide compound.

According to another embodiment of the invention, a method of inducing apoptosis of tumor cells in an individual afflicted with cancer is provided, comprising administering to said individual an effective amount of at least one N-(aryl)-2-arylethenesulfonamide compound.

According to another embodiment of the invention, a method of reducing or eliminating the effects of ionizing radiation on normal cells in a subject who has incurred or is at risk for incurring exposure to ionizing radiation is provided. An effective amount of at least one N-(aryl)-2-arylethenesulfonamide compound is administered to the subject prior to or after exposure to ionizing radiation.

A method of safely increasing the dosage of therapeutic ionizing radiation used in the treatment of cancer or other proliferative disorders is also provided. The method comprises administering an effective amount of at least one radioprotective N-(aryl)-2-arylethenesulfonamide compound prior to administration of the therapeutic ionizing radiation, which radioprotective compound induces a temporary radioresistant phenotype in the normal tissue of the subject.

A method for treating a subject who has incurred or is at risk for incurring remediable radiation damage from exposure to ionizing radiation comprises administering an effective amount of at least one radioprotective N-(aryl)-2-arylethenesulfonamide compound prior to or after incurring remedial radiation damage from exposure to ionizing radiation.

For all of the aforementioned therapeutic methods, the administered compound is a compound according to formula I wherein:

$Q_1$ and $Q_2$ are independently selected from the group consisting of substituted and unsubstituted aryl, and substituted and unsubstituted heteroaryl;

R is defined as above;

wherein the substituents for the substituted aryl and substituted heteroaryl groups comprising $Q_1$ are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$acylamino, sulfamyl, acetoxy, di$(C_1-C_6)$alkylamino$(C_2-C_6)$alkoxy, trifluoromethyl and

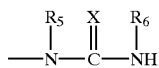

wherein:
X is oxygen or sulfur,
$R^5$ is selected from the group consisting of hydrogen, $(C_1-C_6)$alkyl, $(C_2-C_6)$heteroalkyl, substituted phenyl and unsubstituted phenyl, and $R^6$ is selected from the group consisting of hydrogen, $(C_1-C_6)$alkyl, $(C_2-C_6)$heteroalkyl, substituted aryl, unsubstituted aryl, substituted heteroaryl, unsubstituted heteroaryl, substituted aryl-$(C_1-C_3)$alkyl, unsubstituted aryl-$(C_1-C_3)$alkyl and $(C_1-C_6)$alkoxycarbonyl$(C_1-C_6)$alkylenyl; and wherein the substituents for the substituted aryl and substituted heteroaryl groups comprising $Q_2$, and the substituents for the substituted aryl and substituted heteroaryl groups comprising or included within R, $R^5$ and $R^6$, are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$acylamino, sulfamyl, acetoxy, di$(C_1-C_6)$alkylamino$(C_2-C_6)$alkoxy and trifluoromethyl;

or a pharmaceutically acceptable salt thereof.

The term "acyl" means a radical of the general formula —C(=O)—R, wherein —R is hydrogen, hydrocarbyl, amino or alkoxy. Examples include for example, acetyl (—C(=O)CH$_3$), propionyl (—C(=O)CH$_2$CH$_3$), benzoyl (—C(=O)C$_6$H$_5$). Phenylacetyl (—C(=O)CH$_2$C$_6$H$_5$), carboethoxy (—CO$_2$Et), and dimethylcarbamoyl (—C(=O)N(CH$_3$)$_2$).

The term "aromatic" refers to a carbocycle or heterocycle having one or more polyunsaturated rings having aromatic character (4n+2) delocalized π(pi) electrons).

The term "$(C_2-C_6)$acylamino" means a radical containing a two to six carbon straight or branched chain acyl group attached to a nitrogen atom via the acyl carbonyl carbon. Examples include —NHC(O)CH$_2$CH$_2$CH$_3$ and —NHC(O)CH$_2$CH$_2$ CH$_2$CH$_2$CH$_3$.

The term "alkyl", by itself or as part of another substituent means, unless otherwise stated, a straight or branched chain hydrocarbon radical, including di- and multi-radicals, having the number of carbon atoms designated (i.e. $(C_1-C_6)$ means one to six carbons) and includes straight or branched chain groups. Most preferred is $(C_1-C_3)$alkyl, ethyl or methyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy and the higher homologs and isomers. Preferred are $(C_1-C_3)$alkoxy, ethoxy or methoxy.

The term "alkylenyl" by itself or as part of another substituent means a divalent radical derived from a straight or branched chain alkane having the indicated number of carbon atoms, as exemplified by the four-carbon radical —CH$_2$CH$_2$CH$_2$CH$_2$—.

The term "alkenyl" employed alone or in combination with other terms, means, unless otherwise stated, a stable straight chain or branched monounsaturated or diunsaturated hydrocarbon group having the stated number of carbon atoms. Examples include vinyl, propenyl (allyl), crotyl, isopentenyl, butadienyl, 1,3-pentadienyl, 1,4-pentadienyl, and the higher homologs and isomers. A divalent radical derived from an alkene is exemplified by —CH=CH—CH$_2$—.

The term "carboxy$(C_1-C_3)$alkoxy" means a radical in which the carboxy group —COOH is attached to a carbon of a straight or branched chain alkoxy group containing one to three carbon atoms. The radical thus contains up to four carbon atoms. Examples include HOC(O)CH$_2$CH$_2$CH$_2$O— and HOC(O)CH$_2$CH$_2$O—.

The term "heteroalkyl" by itself or in combination with another term means, unless otherwise stated, a stable straight or branched chain radical consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, and —CH$_2$CH$_2$—S(O)—CH$_3$. Up to two heteroatoms may be consecutive, such as, for example, —CH$_2$—NH—OCH$_3$.

The term "heteroalkenyl" by itself or in combination with another term means, unless otherwise stated, a stable straight or branched chain monounsaturated or diunsaturated hydrocarbon radical consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

The term "hydroxyalkyl" means an alkyl radical wherein one or more of the carbon atoms is substituted with hydroxy. Examples include —CH$_2$CH(OH)CH$_3$ and —CH$_2$CH$_2$OH. The terms "halo" or "halogen" by themselves or as part of another substituent mean, unless otherwise stated, a fluorine, chlorine, bromine, or iodine atom.

The term "(C$_1$-C$_6$)alkoxycarbonyl(C$_1$-C$_6$)alkylenyl" means a group of the formula CH$_3$(CH$_2$)$_p$OC(O)(CH$_2$)$_q$— wherein p is an integer from zero to five and q is an integer from one to six.

The term "di(C$_1$-C$_6$)alkylamino(C$_2$-C$_6$)alkoxy" means (alkyl)$_2$N(CH$_2$)$_n$O— wherein the two alkyl chains connected to the nitrogen atom independently contain from one to six carbon atoms, preferably from one to three carbon atoms, and n is an integer from 2 to 6. Preferably, n is 2 or 3. Most preferably, n is 2, and the alkyl groups are methyl, that is, the group is the dimethylaminoethoxy group, (CH$_3$)$_2$NCH$_2$CH$_2$O—.

The term "phosphonato" means the group —PO(OH)$_2$.

The term "sulfamyl" means the group —SO$_2$NH$_2$.

The term "aryl" employed alone or in combination with other terms, means, unless otherwise stated, a carbocyclic aromatic system containing one or more rings (typically one, two or three rings) wherein such rings may be attached together in a pendent manner or may be fused. Examples include phenyl; anthracyl; and naphthyl, particularly 1-naphthyl and 2-naphthyl.

The term "aryl-(C$_1$-C$_3$)alkyl" means a radical wherein a one to three carbon alkylene chain is attached to an aryl group, e.g., —CH$_2$CH$_2$-phenyl. Similarly, the term "heteroaryl-(C$_1$-C$_3$)alkyl" means a radical wherein a one to three carbon alkylene chain is attached to a heteroaryl group, e.g., —CH$_2$CH$_2$-pyridyl. The term "substituted aryl-(C$_1$-C$_3$)alkyl" means an aryl-(C$_1$-C$_3$)alky radical in which the aryl group is substituted. The term "substituted heteroaryl-(C$_1$-C$_3$)alkyl" means a heteroaryl-(C$_1$-C$_3$)alky radical in which the heteroaryl group is substituted.

The term "heteroaryl" by itself or as part of another substituent means, unless otherwise stated, an unsubstituted or substituted, stable, mono- or multicyclic heterocyclic aromatic ring system which consists of carbon atoms and from one to four heteroatoms selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

Examples of such heteroaryls include benzimidazolyl, particularly 2-benzimidazolyl; benzofuryl, particularly 3-, 4-, 5-, 6- and 7-benzofuryl; 2-benzothiazolyl and 5-benzothiazolyl; benzothienyl, particularly 3-, 4-, 5-, 6-, and 7-benzothienyl; 4-(2-benzyloxazolyl); furyl, particularly 2- and 3-furyl; isoquinolyl, particularly 1- and 5-isoquinolyl; isoxazolyl, particularly 3-, 4- and 5-isoxazolyl; imidazolyl, particularly 2-, -4 and 5-imidazolyl; indolyl, particularly 3-, 4-, 5-, 6- and 7-indolyl; oxazolyl, particularly 2-, 4- and 5-oxazolyl; purinyl; pyrrolyl, particularly 2-pyrrolyl, 3-pyrrolyl; pyrazolyl, particularly 3- and 5-pyrazolyl; pyrazinyl, particularly 2-pyrazinyl; pyridazinyl, particularly 3- and 4-pyridazinyl; pyridyl, particularly 2-, 3- and 4-pyridyl; pyrimidinyl, particularly 2- and 4-pyrimidyl; quinoxalinyl, particularly 2- and 5-quinoxalinyl; quinolinyl, particularly 2- and 3-quinolinyl; 5-tetrazolyl; thiazolyl; particularly 2-thiazolyl, 4-thiazolyl and 5-thiazolyl; thienyl, particularly 2- and 3-thienyl; and 3-(1,2,4-triazolyl). The aforementioned listing of heteroaryl moieties is intended to be representative, not limiting. In another embodiment of the invention, Q$_1$ is independently selected from the group consisting of substituted and unsubstituted aryl, and substituted and unsubstituted heteroaryl, provided that Q$_1$, is not 2-thiazolyl. In a further embodiment of the invention, Q$_1$ is independently selected from the group consisting of substituted and unsubstituted aryl, and substituted and unsubstituted heteroaryl, provided that Q$_1$ is not 2-thiazolyl, 4-thiazolyl or 5-thiazolyl.

The term "substituted" means that an atom or group of atoms has replaced hydrogen as the substituent attached to another group. For aryl and heteroaryl groups, the "substituted" is meant any level of substitution, namely mono-, di-, tri-, tetra-, or penta-substitution. The substituents are independently selected.

For purposes of this disclosure, the term aryl in the expression "N-(aryl)-2-arylethenesulfonamide" is deemed to include both "aryl" and "heteroaryl" radicals, either substituted or unsubstituted, unless otherwise indicated.

The term "subject" or "individual" includes human beings and non-human animals. With respect to the disclosed radioprotective methods, these terms further refer to an organism which is scheduled to incur, is at risk for incurring, or has incurred, exposure to ionizing radiation.

As used herein, "ionizing radiation" is radiation of sufficient energy that, when absorbed by cells and tissues, induces formation of reactive oxygen species and DNA damage. This type of radiation includes X-rays, gamma rays, and particle bombardment (e.g., neutron beam, electron beam, protons, mesons and others), and is used for medical testing and treatment, scientific purposes, industrial testing, manufacturing and sterilization, weapons and weapons development, and many other uses. Radiation is typically measured in units of absorbed dose, such as the rad or gray (Gy), or in units of dose equivalence, such as the rem or sievert (Sv). The relationship between these units is given below:

| rad and gray (Gy) | rem and sievert (Sv) |
|---|---|
| 1 rad = 0.01 Gy | 1 rem = 0.01 Sv |

The Sv is the Gy dosage multiplied by a factor that includes tissue damage done. For example, penetrating ionizing radiation (e.g., gamma and beta radiation) have a factor of about 1, so 1 Sv=~1 Gy. Alpha rays have a factor of 20, so 1 Gy of alpha radiation=20 Sv.

By "effective amount of ionizing radiation" is meant an amount of ionizing radiation effective in killing, or reducing the proliferation, of abnormally proliferating cells in a subject. As used with respect to bone marrow purging, "effective amount of ionizing radiation" means an amount of ionizing radiation effective in killing, or in reducing the proliferation, of malignant cells in a bone marrow sample removed from a subject.

By "acute exposure to ionizing radiation" or "acute dose of ionizing radiation" is meant a dose of ionizing radiation absorbed by a subject in less than 24 hours. The acute dose may be localized, as in radiotherapy techniques, or may be absorbed by the subjects entire body. Acute doses are typically above 10,000 millirem (0.1 Gy), but may be lower.

By "chronic exposure to ionizing radiation" or "chronic dose of ionizing radiation" is meant a dose of ionizing radiation absorbed by a subject over a period greater than 24 hours. The dose may be intermittent or continuous, and may be localized or absorbed by the subject's entire body. Chronic doses are typically less than 10,000 millirem (0.1 Gy), but may be higher.

By "effective amount of radioprotective N-(aryl)-2-arylethenesulfonamide compound" is meant an amount of compound effective to reduce or eliminate the toxicity associated with radiation in normal cells of the subject, and also to impart a direct cytotoxic effect to abnormally proliferating cells in the subject. As used with respect to bone marrow purging, "effective amount of the radioprotective N-(aryl)-2-arylethenesulfonamide compound" means an amount of compound effective to reduce or eliminate the toxicity associated with radiation in bone marrow removed from a subject, and also to impart a direct cytotoxic effect to malignant cells in the bone marrow removed from the subject.

By "at risk of incurring exposure to ionizing radiation" is meant that a subject may advertently (such as by scheduled radiotherapy sessions) or inadvertently be exposed to ionizing radiation in the future. Inadvertent exposure includes accidental or unplanned environmental or occupational exposure.

DETAILED DESCRIPTION OF THE INVENTION

Figure 1:
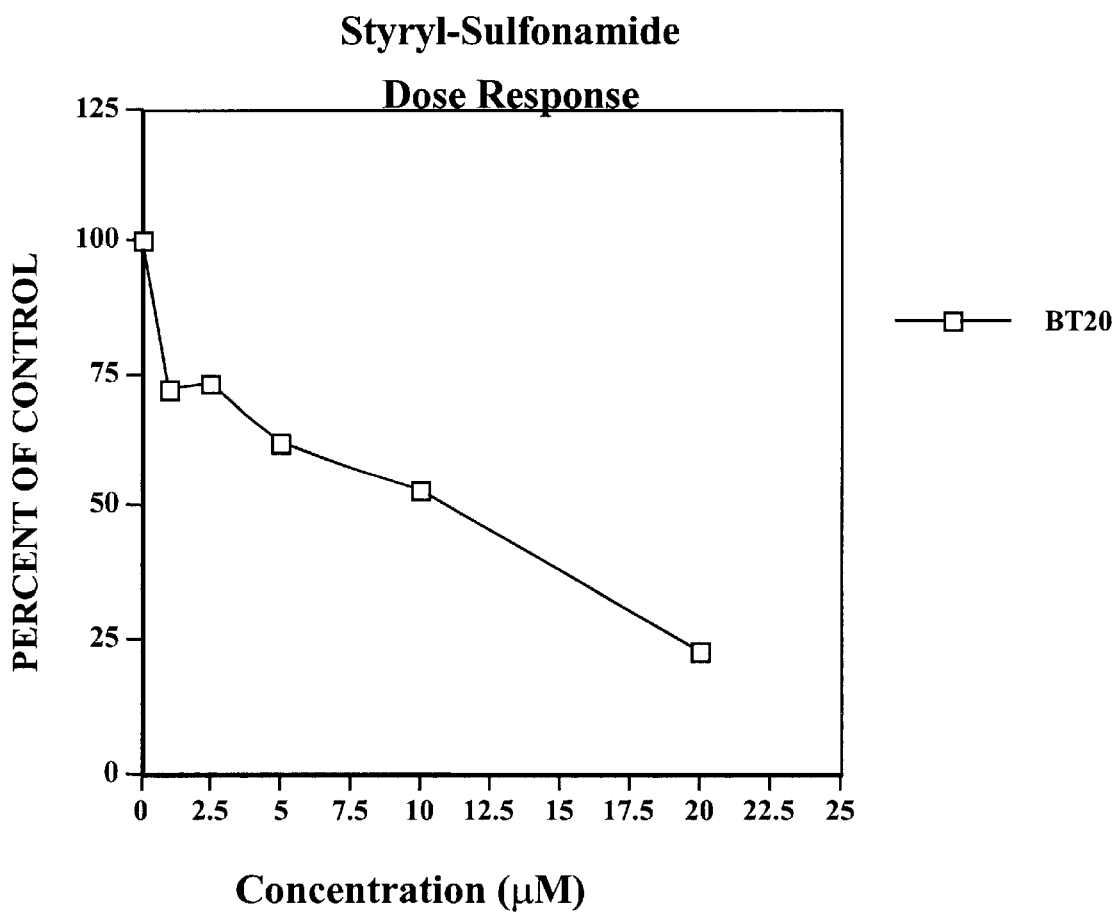
FIG. 1 is a plot of the growth inhibition effect of (E)-4-methoxystyryl-N-4-fluorophenyl sulfonamide on the breast tumor cell line BT20, as a function of concentration.

According to the present invention, N-(aryl)-2-arylethenesulfonamides and pharmaceutically acceptable salts thereof selectively inhibit proliferation of cancer cells, and kill various tumor cell types without killing normal cells. Cells are killed at concentrations where normal cells may be temporarily growth-arrested but not killed.

The N-(aryl)-2-arylethenesulfonamides compounds of the invention have been shown to inhibit the proliferation of tumor cells, and for some compounds, induce cell death. Cell death results from the induction of apoptosis. The compounds are believed effective against a broad range of tumor types, including but not limited to the following: breast, prostate, ovarian, lung, colorectal, brain (i.e, glioma) and renal. The compounds are also effective against leukemic cells.

The N-(aryl)-2-arylethenesulfonamides compounds are also believed useful in the treatment of non-cancer proliferative disorders, including but not limited to the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

The N-(aryl)-2-arylethenesulfonamides also protect normal cells and tissues from the effects of acute and chronic exposure to ionizing radiation.

Subjects may be exposed to ionizing radiation when undergoing therapeutic irradiation for the treatment of the above proliferative disorders. The N-(aryl)-2-arylethenesulfonamides are effective in protecting normal cells during therapeutic irradiation of abnormal tissues. The compounds are also believed useful in protecting normal cells during radiation treatment for leukemia, especially in the purging of malignant cells from autologous bone marrow grafts with ionizing radiation.

According to the invention, therapeutic ionizing radiation may be administered to a subject on any schedule and in any dose consistent with the prescribed course of treatment, as long as the N-(aryl)-2-arylethenesulfonamide radioprotectant compound is administered prior to the radiation. The course of treatment differs from subject to subject, and those of ordinary skill in the art can readily determine the appropriate dose and schedule of therapeutic radiation in a given clinical situation.

In some embodiments of the invention, R in formula I may be selected from hydrogen and $(C_1-C_6)$alkyl, particularly $(C_1-C_3)$alkyl, and even more particularly ethyl or methyl. In other embodiments, $Q_1$ and $Q_2$ are selected from substituted and unsubstituted phenyl, particularly mono-, di- or trisubstituted phenyl. In certain embodiments, at least one of $Q_1$ and $Q_2$ is at least trisubstituted, at least tetrasubstituted, or even pentasubstituted.

According to another embodiment of the invention of formula I, $Q_1$ and $Q_2$ are optionally substituted phenyl. In some embodiments, the substituents are selected from halogen, $(C_1-C_6)$alkyl, $(C_1-C_6)$alkoxy, nitro, hydroxy and sulfamyl. In certain sub-embodiments, at least one of $Q_1$ or $Q_2$ is substituted in at least the 4-position, or both of $Q_1$, and $Q_2$ are substituted at the 4-position. According to certain other sub-embodiments, the substitutions are selected from the group consisting of halogen, $(C_1-C_6)$alkyl and $(C_1-C_6)$alkoxy.

According to another sub-embodiment of the invention, a compound has the formula II:

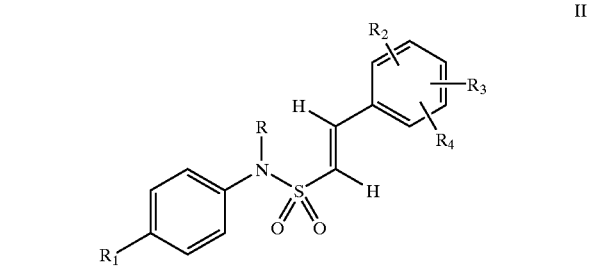

wherein $R_1$ is selected from the group consisting of halogen, $(C_1-C_6)$alkyl, $(C_1-C_6)$alkoxy, nitro, cyano, carboxy, carboxy($C_1$–$C_3$)alkoxy, hydroxy, ($C_2$–$C_6$)hydroxyalkyl, phosphonato, amino, ($C_1$–$C_6$)acylamino, sulfamyl, acetoxy, di($C_1$–$C_6$)alkylamino($C_2$–$C_6$)alkoxy and trifluoromethyl; R is defined as above; and $R^2$, $R^3$ and $R^4$, are independently selected from the group consisting of ($C_1$–$C_6$)alkoxy. A preferred pattern of substitution for $R^2$/$R^3$/$R^4$ is 2,4,6, that is, the compound has the formula IIa:

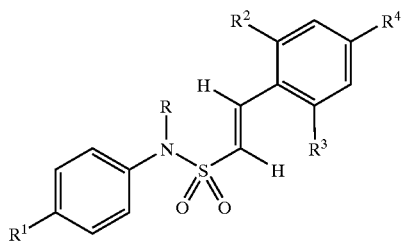

IIa wherein $R^1$, $R^2$, $R^3$ and $R^4$ are defined as for formula II.

In some embodiments of formula II and IIa, $R^1$ is selected from the group consisting of halogen, ($C_1$–$C_6$)alkyl, ($C_1$–$C_6$)alkoxy, nitro, hydroxy and sulfamyl.

According to another sub-embodiment, $Q_1$ and $Q_2$ are optionally substituted phenyl, and at least one of $Q_1$ or $Q_2$ is at least tetrasubstituted. In other embodiments, at least one of $Q_1$ and $Q_2$ is pentasubstituted, e.g. particularly with halogen, most preferably with fluorine.

Compounds having a carbon-carbon double bond are characterized by cis-trans isomerism. Such compounds are named according to the Cahn-Ingold-Prelog system, the IUPAC 1974 Recommendations, Section E: Stereochemistry, in *Nomenclature of Organic Chemistry*, John Wiley & Sons, Inc., New York, N.Y., 4th ed., 1992, p. 127–138. Steric relations around a double bond are designated as "Z" or "E". The compounds of the present invention have the "E" configuration.

The N-(aryl)-2-arylethenesulfonamides may be prepared by one of two methods. In the synthesis methods to follow, reference to "aryl" is intended to include substituted and unsubstituted aryl, and also substituted and unsubstituted heteroaryl.

According to Scheme 1, the arylethene A, where $Q_2$ is substituted or unsubstituted aryl, is reacted with sulfonyl chloride in the presence of a nonprotic solvent to form the corresponding arylethene sulfonyl chloride B. Appropriate solvents for this reaction include, for example, dimethylformamide, chloroform and benzene. The arylethene sulfonyl chloride B is then reacted in a nonprotic solvent in the presence of a base with the N-aryl compound C, wherein $Q_1$ is substituted or unsubstituted aryl, to obtain the desired N-(aryl)-2-arylethenesulfonamide of formula I. The arylethene sulfonyl chloride is highly reactive with N-aryl compound C, and HCl is a byproduct of the reaction. The base is present in the solvent to serve as a scavenger for the produced HCl. The same compound may serve as both the nonprotic solvent and the base. Such dual-function solvents include, for example, pyridine, substituted pyridines, trimethylamine and triethylamine.

Scheme 1
Synthesis of olefinic sulfonyl chlorides and reaction with aryl amines to form compounds of formula I

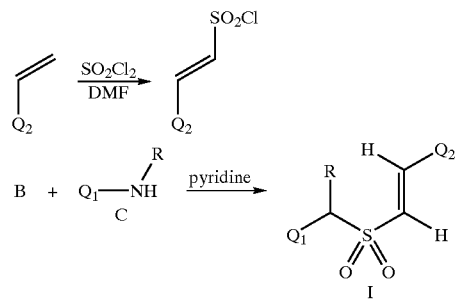

According to Scheme 2, a Knoevenagel-type condensation according to Oliver et al., *Synthesis* 321–322 (May 1975) is utilized, relying on the condensation of an arylaminosulfonylacetic acid intermediate G with an appropriate aryl aldehyde H. The entire disclosure of Oliver et al. is incorporated herein by reference.

Scheme 2
Synthesis of compounds of formula I

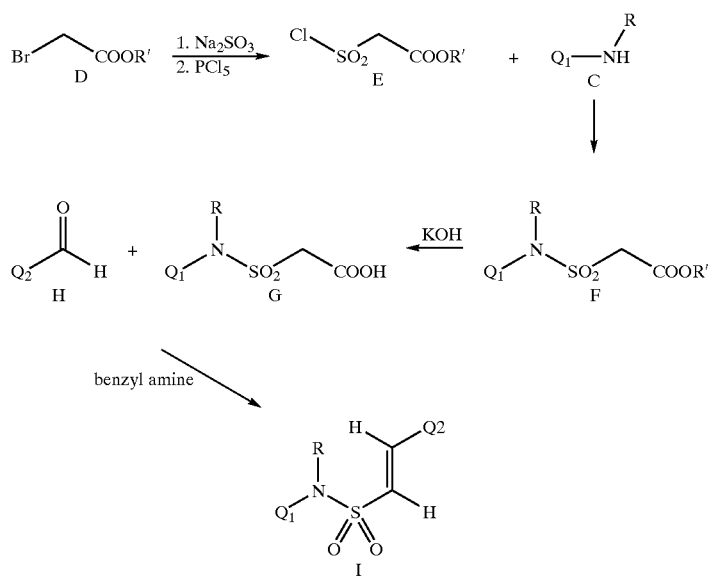

A methyl (or ethyl) β-chlorosulfonylacetate intermediate E is prepared from methyl (or ethyl) bromoacetate (R'=methyl or ethyl). To do this, methyl (or ethyl) bromoacetate is reacted with sodium sulfate to form the sodium sulfoacetate intermediate $Na_2OSO_2CH_2CO_2R'$. Potassium sulfate may be used as a substitute for sodium sulfate. The sodium sulfoacetate intermediate is then reacted with a chlorinating agent, preferably $PCl_5$, to form the methyl (or ethyl) β-chlorosulfonylacetate intermediate E. Reaction of intermediate E with the aromatic amine C yields the arylaminosulfonylacetate intermediate F. The latter reaction is conducted in a nonprotic solvent in the presence of a base. The same compound may serve as both the nonprotic solvent and the base. Such dual-function solvents include, for example, pyridine, substituted pyridines, trimethylamine and triethylamine. The arylaminosulfonylacetate F is then converted to the corresponding arylaminosulfonylacetic acid compound G by any base capable of hydrolyzing the ester function of F to an acid. Such bases include KOH and NaOH, for example. In the final step, the arylaminosulfonylacetic acid compound is condensed with arylaldehyde H in the presence of a basic catalyst via a Knoevenagel reaction and decarboxylation of an intermediate. Basic catalysts include, for example, pyridine and benzylamine. The reaction yields the desired N-(aryl)-2-arylethenesulfonamide of formula I.

The following are more detailed procedures for the preparation of the formula I compounds, according to either Scheme 1 (General Procedure 1) or Scheme 2 (General Procedure 2).

General Procedure 1

A. Synthesis of (E)—$Q_2$—CH=CH—$SO_2Cl$

To a stirred solution of an arylethene A (0.1 mol) in dimethyl formamide (30 mL), sulfuryl chloride (0.2 mol) is added dropwise for 30 minutes under nitrogen atmosphere. After the addition is complete, the solution is stirred further for 5 hours under nitrogen atmosphere. The reaction mixture is then slowly poured into cold water (250 mL) and the precipitated material is extracted with diethyl ether. Evaporation of the dried ethereal layer yields the corresponding sulfonyl chloride (E)—$Q_2$—CH=CH—$SO_2Cl$ (B).

B. Condensation of (E)—$Q_2$—CH=CH—$SO_2Cl$ with arylamine

The N-aryl compound C (10 mmol) and sulfonyl chloride B (10 mmol) are dissolved in 15 mL of pyridine under nitrogen. The mixture is stirred for 6 hours at room temperature, and the solvent is removed at aspirator pressure. Water (100 mL) is added to the residue and the product is filtered. Recrystallization of the product gives pure N-(aryl)-2-arylethenesulfonamide of formula I.

General Procedure 2

A. Synthesis of Sodium Ethyl or Methyl Sulfoacetate

A solution of ethyl or methyl bromoacetate (0.1 mol) in ethanol (50 mL) is added dropwise to a stirred cold solution of sodium sulfite (0.1 mol) in water (100 mL). After the addition is complete, the mixture is heated briefly to 50° C. and then concentrated to dryness. The solid residue is extracted with boiling 2:1 acetic acid/ethyl acetate (200 mL) and the hot solution is filtered and chilled overnight. The sodium methyl or ethyl sulfoacetate obtained as a white solid is collected by filtration.

B. Synthesis of Ethyl or Methyl Arylaminosulfonylacetate

Sodium methyl or ethyl sulfoacetate (0.1 mol) and phosphorus (V) chloride (0.11 mol) are separately pulverized and then combined in a flask equipped with a condenser and drying tube. After swirling a few minutes, an exothermic reaction occurs. After the reaction subsides, the flask is warmed on a steam bath for 1 hour and then phosphoryl chloride is removed in vacuo. A portion of benzene is added and the resulting solution is filtered and evaporated to yield ethyl or methyl-chlorosulfonyl acetate (E) solution. Benzene (50 mL) is added to this clear oil and the solution is stirred and cooled. To this solution, an N-aryl compound C and triethylamine (10 mL) in benzene (50 mL) is added dropwise. After the addition is complete, the mixture is warmed gently for 5 minutes, then is cooled and filtered. The filtrate is washed with water, dilute hydrochloric acid, aqueous sodium hydrogen carbonate and aqueous sodium chloride. After drying the solvent is removed to give crude ethyl or methyl arylaminosulfonylacetate F. Recrystallization from benzene yields a pure compound.

C. Synthesis of Arylaminosulfonylacetic Acid

The ethyl or methyl arylaminosulfonylacetate F (0.1 mol) is refluxed for 2.5 hours in a solution of potassium hydroxide (15 g) in water (100 mL) and ethanol (40 mL). Charcoal is added and the solution is heated to boiling for 5 minutes, filtered, acidified with hydrochloric acid and extracted with ether. The ether extract is washed with water, dried and evaporated to give the crude arylaminosulfonylacetic acid G which is purified by recrystallization from benzene.

D. Condensation of Arylaminosulfonylacetic Acid with Arylaldehyde

A solution of the arylaminosulfonylacetic acid G (10 mmol), arylaldehyde H (10 mmol), pyridine (1 mL) and ammonium acetate (250 mg) are refluxed for 22 hours in toluene with azeotropic removal of water. The solution is cooled, washed with water, dilute hydrochloric acid and aqueous sodium hydrogen carbonate and then is extracted with 10% potassium hydroxide. The two-phase aqueous extract is washed with ether and acidified with hydrochloric acid. Evaporation of the ether extract yields crude N-(aryl)-2-arylethenesulfonamide of formula I. Recrystallization from appropriate solvent provides an analytical sample.

N-(aryl)-2-arylethenesulfonamides according to formula I wherein the aryl nucleus of $Q_1$ is substituted with the group

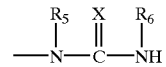

wherein X is sulfur or oxygen and $R^5$ and $R^6$ are defined as above, are prepared according to a variation of the above procedure. Accordingly, an aryl intermediate which is substituted with at least one amino and at least one nitro group, preferably a phenyl intermediate of the formula III

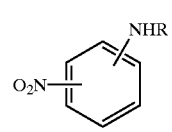

III wherein R is defined as above, and wherein the phenyl ring may be further substituted as described above, is reacted with the sulfonyl chloride B as in Scheme 1 to obtain the desired N-(nitroaryl)-2-arylethenesulfonamide IV:

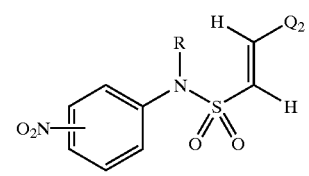

IV

The nitro group is reduced to an amino group by hydrogenation with a catalyst of palladium on carbon, for example, to form amino intermediate V:

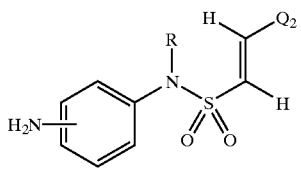

Alternatively, the amine intermediate Va is prepared:

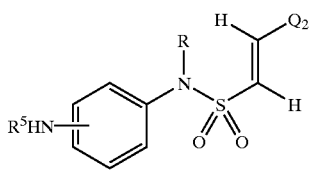

wherein $R_5$ is selected from the group consisting of hydrogen, $(C_1-C_6)$alkyl, $(C_2-C_6)$heteroalkyl and substituted or unsubstituted phenyl. The amino group is then made to react with a compound of formula VI

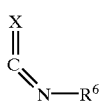

wherein X is oxygen or sulfur, and $R^6$ is selected from the group consisting of hydrogen, $(C_1-C_6)$alkyl, $(C_2-C_6)$ heteroalkyl, substituted aryl, unsubstituted aryl, substituted heteroaryl, unsubstituted heteroaryl, substituted aryl-$(C_1-C_3)$alkyl, unsubstituted aryl-$(C_1-C_3)$alkyl and $(C_1-C_6)$ alkoxycarbonyl$(C_1-C_6)$alkylenyl, to form the urea/thiourea derivative of formula VII:

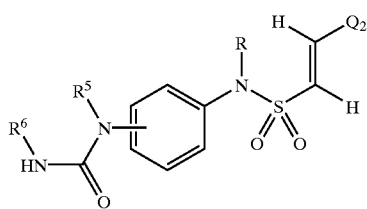

The reaction may be carried out, for example, by dissolving the compound of formula VI in deionized water and adding an approximately equimolar amount thereof to the intermediate V or Va dissolved in an appropriate solvent, such as glacial acetic acid. The reaction mixture is stirred at room temperature for three hours. The reaction mixture is then poured into deionized water and extracted 3 times with ethyl acetate. The resulting combined organic layers are washed with saturated $NaHCO_3$ and saturated brine. The solvent is dried over $MgSO_4$, filtered, and concentrated under reduced pressure. The resulting solid is recrystalized from hot ethyl acetate/hexane, for example, to give the sulfonamide VII.

The compounds of the present invention may take the form or pharmaceutically acceptable salts. The term "pharmaceutically acceptable salts", embraces salts commonly used to form alkali metal salts and to form addition salts of free acids or free bases. The nature of the salt is not critical, provided that it is pharmaceutically-acceptable. Suitable pharmaceutically acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid. Suitable pharmaceutically acceptable base addition salts of compounds of formula I include metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I by reacting, for example, the appropriate acid or base with the compound of formula I.

The compounds of the invention may be administered to individuals (mammals, including animals and humans) afflicted with cancer.

The compounds are also useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Such disorders include, but are not limited to, the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

For treating proliferative disorders, the specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.05 to about 50 mg/kg/day may be utilized. Higher or lower doses are also contemplated.

For radioprotective administration, the specific dose and schedule of N-(aryl)-2-arylethenesulfonamide to obtain the radioprotective benefit will, of course, be determined by the particular circumstances of the individual patient including, the size, weight, age and sex of the patient, the nature and stage of the disease being treated, the aggressiveness of the disease, and the route of administration, and the specific toxicity of the radiation. For example, a daily dosage of from about 0.01 to about 150 mg/kg/day may be utilized, more preferably from about 0.05 to about 50 mg/kg/day. Particularly preferred are doses from about 1.0 to about 10.0 mg/kg/day, for example, a dose of about 7.0 mg/kg/day. The dose may be given over multiple administrations, for example, two administrations of 3.5 mg/kg. Higher or lower doses are also contemplated.

For radioprotective administration, the N-(aryl)-2-arylethenesulfonamide should be administered far enough in advance of the therapeutic radiation such that the compound is able to reach the normal cells of the subject in sufficient concentration to exert a radioprotective effect on the normal cells. The compound may be administered as much as about 24 hours, preferably no more than about 18 hours, prior to administration of the radiation. In one embodiment, the N-(aryl)-2-arylethenesulfonamide is administered at least about 6–12 hours before administration of the therapeutic radiation. Most preferably, the compound is administered once at about 18 hours and again at about 6 hours before the radiation exposure. One or more N-(aryl)-2-arylethenesulfonamides may be administered simultaneously, or different N-(aryl)-2-arylethenesulfonamides may be administered at different times during the treatment.

Where the therapeutic radiation is administered in serial fashion, it is preferable to intercalate the administration of one or more N-(aryl)-2-arylethenesulfonamides within the schedule of radiation treatments. As above, different N-(aryl)-2-arylethenesulfonamides may be administered either simultaneously or at different times during the treatment. Preferably, an about 24 hour period separates administration of the radioprotective compound and the therapeutic radiation. More preferably, the administration of the radioprotective N-(aryl)-2-arylethenesulfonamide and the therapeutic radiation is separated by about 6 to 18 hours. This strategy will yield significant reduction of radiation-induced side effects without affecting the anticancer activity of the therapeutic radiation.

For example, therapeutic radiation at a dose of 0.1 Gy may be given daily for five consecutive days, with a two day rest, for a total period of 6–8 weeks. One or more N-(aryl)-2-arylethenesulfonamides may be administered to the subject 18 hours previous to each round of radiation. It should be pointed out, however, that more aggressive treatment schedules, i.e., delivery of a higher dosage, is contemplated according to the present invention due to the protection of the normal cells afforded by the N-(aryl)-2-arylethenesulfonamides. Thus, the radioprotective effect of the compound increases the therapeutic index of the therapeutic radiation, and may permit the physician to safely increase the dosage of therapeutic radiation above presently recommended levels without risking increased damage to the surrounding normal cells and tissues.

The N-(aryl)-2-arylethenesulfonamides of the invention are further useful in protecting normal bone marrow cells from radiologic treatments designed to destroy hematologic neoplastic cells or tumor cells which have metastasized into the bone marrow. Such cells include, for example, myeloid leukemia cells. The appearance of these cells in the bone marrow and elsewhere in the body is associated with various disease conditions, such as the French-American-British (FAB) subtypes of acute myelogenous leukemias (AML), chronic myeloid leukemia (CML), and acute lymphocytic leukemia (ALL). CML, in particular, is characterized by abnormal proliferation of immature granulocytes (e.g., neutrophils, eosinophils, and basophils) in the blood, bone marrow, spleen, liver, and other tissues and accumulation of granulocytic precursors in these tissues. The subject who presents with such symptoms will typically have more than 20,000 white blood cells per microliter of blood, and the count may exceed 400,000. Virtually all CML patients will develop "blast crisis", the terminal stage of the disease during which immature blast cells rapidly proliferate, leading to death.

Other subjects suffer from metastatic tumors, and require treatment with total body irradiation (TBI). Because TBI will also kill the subject's hematopoietic cells, a portion of the subject's bone marrow is removed prior to irradiation for subsequent reimplantation. However, metastatic tumor cells are likely present in the bone marrow, and reimplantation often results in a relapse of the cancer within a short time.

Subjects presenting with neoplastic diseases of the bone marrow or metastatic tumors may be treated by removing a portion of the bone marrow (also called "harvesting"), purging the harvested bone marrow of malignant stem cells, and reimplanting the purged bone marrow. Preferably, the subject is treated with radiation or some other anti-cancer therapy before the autologous purged bone marrow is reimplanted.

Thus, the invention provides a method of reducing the number of malignant cells in bone marrow, comprising the steps of removing a portion of the subject's bone marrow, administering an effective amount of at least one N-(aryl)-2-arylethenesulfonamide and irradiating the treated bone marrow with a sufficient dose of ionizing radiation such that malignant cells in the bone marrow are killed. As used herein, "malignant cell" means any uncontrollably proliferating cell, such a tumor cell or neoplastic cell. The N-(aryl)-2-arylethenesulfonamides protect the normal hematopoietic cells present in the bone marrow from the deleterious effects of the ionizing radiation. The N-(aryl)-2-arylethenesulfonamides also exhibit a direct killing effect on the malignant cells. The number of malignant cells in the bone marrow is significantly reduced prior to reimplantation, thus minimizing the occurrence of a relapse.

Preferably, each N-(aryl)-2-arylethenesulfonamide is administered in a concentration from about 0.25 to about 100 micromolar; more preferably, from about 1.0 to about 50 micromolar; in particular from about 2.0 to about 25 micromolar. Particularly preferred concentrations are 0.5, 1.0 and 2.5 micromolar and 5, 10 and 20 micromolar. Higher or lower concentrations may also be used.

The N-(aryl)-2-arylethenesulfonamides may be added directly to the harvested bone marrow, but are preferably dissolved in an organic solvent such as dimethylsulfoxide (DMSO). Pharmaceutical formulations of N-(aryl)-2-arylethenesulfonamides such as are described in more detail below may also be used.

Preferably, the N-(aryl)-2-arylethenesulfonamide is added to the harvested bone marrow about 20 hours prior to radiation exposure, preferably no more than about 24 hours prior to radiation exposure. In one embodiment, the N-(aryl)-2-arylethenesulfonamide is administered to the harvested bone marrow at least about 6 hours before radiation exposure. One or more N-(aryl)-2-arylethenesulfonamides may be administered simultaneously, or different N-(aryl)-2-arylethenesulfonamides may be administered at different times. Other dosage regimens are also contemplated.

If the subject is to be treated with ionizing radiation prior to reimplantation of the purged bone marrow, the subject may be treated with one or more N-(aryl)-2-arylethenesulfonamides prior to receiving the ionizing radiation dose, as described above.

A subject may also be exposed to ionizing radiation from occupation or environmental sources, as discussed in the background section. For purposes of the invention, the source of the radiation is not as important as the type (i.e., acute or chronic) and dose level absorbed by the subject. It is understood that the following discussion encompasses ionizing radiation exposures from both occupational and environmental sources.

Subjects suffering from effects of acute or chronic exposure to ionizing radiation that are not immediately fatal are said to have remediable radiation damage. Such remediable radiation damage can be reduced or eliminated by the compounds and methods of the present invention.

An acute dose of ionizing radiation which may cause remediable radiation damage includes a localized or whole body dose, for example, between about 10,000 millirem (0.1 Gy) and about 1,000,000 millirem (10 Gy) in 24 hours or less, preferably between about 25,000 millirem (0.25 Gy) and about 200,000 (2 Gy) in 24 hours or less, and more preferably between about 100,000 millirem (1 Gy) and about 150,000 millirem (1.5 Gy) in 24 hours or less.

A chronic dose of ionizing radiation which may cause remediable radiation damage includes a whole body dose of about 100 millirem (0.001 Gy) to about 10,000 millirem (0.1 Gy), preferably a dose between about 1000 millirem (0.01 Gy) and about 5000 millirem (0.05 Gy) over a period greater than 24 hours, or a localized dose of 15,000 millirem (0.15 Gy) to 50,000 millirem (0.5 Gy) over a period greater than 24 hours.

The invention therefore provides a method for treating individuals who have incurred remediable radiation damage from acute or chronic exposure to ionizing radiation, comprising reducing or eliminating the cytotoxic effects of radiation exposure on normal cells and tissues by administering an effective amount of at least one radioprotective N-(aryl)-2-arylethenesulfonamide compound. The compound is preferably administered in as short a time as possible following radiation exposure, for example between 0–6 hours following exposure.

Remediable radiation damage may take the form of cytotoxic and genotoxic (i.e., adverse genetic) effects in the subject. In another embodiment, there is therefore provided a method of reducing or eliminating the cytotoxic and genotoxic effects of radiation exposure on normal cells and tissues, comprising administering an effective amount of at least one radioprotective N-(aryl)-2-arylethenesulfonamide compound prior to acute or chronic radiation exposure. The N-(aryl)-2-arylethenesulfonamide may be administered, for example about 24 hours prior to radiation exposure, preferably no more than about 18 hours prior to radiation exposure. In one embodiment, the N-(aryl)-2-arylethenesulfonamide is administered at least about 6 hours before radiation exposure. Most preferably, the N-(aryl)-2-arylethenesulfonamide is administered at about 18 and again at about 6 hours before the radiation exposure. One or more N-(aryl)-2-arylethenesulfonamides may be administered simultaneously, or different N-(aryl)-2-arylethenesulfonamides may be administered at different times.

When multiple acute exposures are anticipated, the radioprotective may be administered multiple times. For example, if fire or rescue personnel must enter contaminated areas multiple times, N-(aryl)-2-arylethenesulfonamides may be administered prior to each exposure. Preferably, an about 24 hour period separates administration of the compound and the radiation exposure. More preferably, the administration of N-(aryl)-2-arylethenesulfonamide and the radiation exposure is separated by about 6 to 18 hours. It is also contemplated that a worker in a nuclear power plant may be administered an effective amount of N-(aryl)-2-arylethenesulfonamide prior to beginning each shift, to reduce or eliminate the effects of exposure to ionizing radiation.

If a subject is anticipating chronic exposure to ionizing radiation, the N-(aryl)-2-arylethenesulfonamide may be administered periodically throughout the duration of anticipated exposure. For example, a nuclear power plant worker or a soldier operating in a forward area contaminated with radioactive fallout may be given the radioprotective compound every 24 hours, preferably every 6–18 hours, in order to mitigate the effects of radiation damage. Likewise, N-(aryl)-2-arylethenesulfonamide compound may be periodically administered to civilians living in areas contaminated by radioactive fallout until the area is decontaminated or the civilians are removed to a safer environment.

As used herein, "administered" means the act of making the N-(aryl)-2-arylethenesulfonamide compound available to the subject such that a pharmacologic effect is obtained. For administration of drug for radioprotection, the pharmacologic effect may manifest as the absence of expected physiologic or clinical symptoms at a certain level of radiation exposure. One skilled in the art may readily determine the presence or absence of radiation-induced effects, by well-known laboratory and clinical methods. The N-(aryl)-2-arylethenesulfonamide compound may thus be administered by any route which is sufficient to bring about the desired radioprotective effect in the patient.

The N-(aryl)-2-arylethenesulfonamide compounds may be administered for therapeutic effect by any route, for example enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical or subcutaneous administration. Also contemplated within the scope of the invention is the instillation of drug in the body of the patient in a controlled formulation, with systemic or local release of the drug to occur at a later time. For example, a depot of N-(aryl)-2-arylethenesulfonamide may be administered to the patient more than 24 hours before the administration of radiation. Preferably, at least a portion of the compound is retained in the depot and not released until an about 6–18 hour window prior to the radiation exposure. For anticancer use, the drug may similarly be localized in a depot for controlled release to the circulation, or local site of tumor growth.

The compounds of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agent. Stabilizing agents, antioxidizing agents and preservatives may also be added.

Suitable antioxidizing agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The practice of the invention is illustrated by the following non-limiting examples. In each of Examples 1–17, the starting (E)—Q$_2$—CH═CH—SO$_2$Cl compound was made according to part A of General Procedure 1, above. The synthesized compounds are tabulated in Table 4.

TABLE 4

IV

| Example # | X | Y | R |
|---|---|---|---|
| 1 | 4-Cl | H | H |
| 2 | 3-F, 4-OCH$_3$ | 4-Cl | H |
| 3 | 4-F | 4-Cl | H |
| 4 | 4-F | 4-OCH$_3$ | H |
| 5 | 3-F, 4-OCH$_3$ | 4-OCH$_3$ | H |
| 6 | 4-F | H | H |
| 7 | H | 4-OCH$_3$ | CH$_3$ |
| 8 | 3-Cl | 4-Cl | H |
| 9 | 2-Cl | 4-Cl | H |
| 10 | 4-F | 4-OCH$_3$ | H |
| 11 | 4-Cl | 4-F | H |
| 12 | 2,4,6-(OCH$_3$)$_3$ | 4-OCH$_3$ | H |
| 13 | 2,3,4,5,6-F$_5$ | 4-OCH$_3$ | H |
| 14 | 2,3,4,5,6-F$_5$ | H | H |
| 15 | 2,3,4,5,6-F$_5$ | 4-F | H |
| 16 | 4-SO$_2$NH$_2$ | H | H |
| 17 | 4-SO$_2$NH$_2$ | 4-OCH$_3$ | H |

EXAMPLE 1

(E)-styryl-N-4-chlorophenyl sulfonamide

A solution of (E)-styrylsulfonyl chloride (10 mmol) and 4-chloroaniline (10 mmol) was subjected to General Procedure 1, part B. The title compound, melting point 107–109° C. was obtained in 56% yield.

EXAMPLE 2

(E)-4-chlorostyryl-N-3-fluoro-4-methoxyphenyl sulfonamide

A solution of (E)-4-chlorostyrylsulfonyl chloride (10 mmol) and 3-fluoro-4-methoxyaniline (10 mmol) was subjected to General Procedure 1, part B. The title compound, melting point 101–102° C. was obtained in 58% yield.

EXAMPLE 3

(E)-4-chlorostyryl-N-4-fluorophenyl sulfonamide

A solution of (E)-4-chlorostyrylsulfonyl chloride (10 mmol) and 4-fluoroaniline (10 mmol) was subjected to General Procedure 1, part B. The title compound, melting point 105–107° C., was obtained in 68.5% yield.

EXAMPLE 4

(E)-4-methoxystyryl-N-4-fluorophenyl sulfonamide

A solution of (E)-4-methoxystyrylsulfonyl chloride (10 mmol) and 4-fluoroaniline (10 mmol) was subjected to General Procedure 1, part B. The title compound, melting point 115–117° C., was obtained 86.4% yield.

EXAMPLE 5

(E)-4-methoxystyryl-N-3-fluoro4-methoxyphenyl sulfonamide

A solution of (E)-4-methoxystyrylsulfonyl chloride (10 mmol) and 3-flouro-4-methoxyaniline (10 mmol) was subjected to General Procedure 1, part B. The title compound, melting point 151–153° C., was obtained 80% yield.

EXAMPLE 6

(E)-styryl-N-4-fluorophenyl sulfonamide

A solution of (E)-styrylsulfonyl chloride (10 mmol) and 4-fluoroaniline (10 mmol) was subjected to General Procedure 1, part B. The title compound, melting point 83–85° C., was obtained 58.7% yield.

EXAMPLE 7

(E)-4-methoxystyryl-N-methyl-N-phenyl sulfonamide

A solution of (E)-4-methoxystyrylsulfonyl chloride (10 mmol) and N-methyl aniline (10 mmol) was subjected to General Procedure 1, part B. The title compound, melting point 126–129° C., was obtained 80.9% yield.

EXAMPLE 8

(E)-4-chlorostyryl-N-3-chlorophenyl sulfonamide

A solution of (E)-4-chlorostyrylsulfonyl chloride (10 mmol) and 3-chloroaniline (10 mmol) was subjected to General Procedure 1, part B. The title compound, melting point 118–120° C., was obtained in 31.8% yield.

EXAMPLE 9

(E)-4-chlorostyryl-N-2-chlorophenyl sulfonamide

A solution of (E)-4-chlorostyrylsulfonyl chloride (10 mmol) and 2-chloroaniline (10 mmol) was subjected to General Procedure 1, part B. The title compound, melting point 107–109° C., was obtained in 57.8% yield.

EXAMPLE 10

(E)-4-methoxystyryl-N-4-fluorophenyl sulfonamide

A solution of (E)-4-methoxystyrylsulfonyl chloride (10 mmol) and 4-fluoroaniline (10 mmol) was subjected to General Procedure 1, part B. The title compound was obtained in 60.3% yield.

EXAMPLE 11

(E)-4-fluorostyryl-N-4-chlorophenyl sulfonamide

A solution of (E)-4-fluorostyrylsulfonyl chloride (10 mmol) and 4-chloroaniline (10 mmol) was subjected to General Procedure 1, part B. The title compound, melting point 126–128° C, was obtained in 81.7% yield.

EXAMPLE 12

(E)-4-methoxystyryl-N-2,4,6-trimethoxyphenyl sulfonamide

A solution of (E)-4-methoxystyrylsulfonyl chloride (10 mmol) and 2,4,6-trimethoxyaniline (10 mmol) was subjected to General Procedure 1, part B. The title compound, melting point 103–106° C., was obtained in 78.7% yield.

EXAMPLE 13

(E)-4-methoxystyryl-N-2,3,4,5,6-pentafluorophenyl sulfonamide

A solution of (E)-4-methoxystyrylsulfonyl chloride (10 mmol) and 2,3,4,5,6-pentafluoroaniline (10 mmol) was subjected to General Procedure 1, part B. The title compound, melting point 58–60° C., was obtained in 41% yield.

EXAMPLE 14

(E)-styryl-N-2,3,4,5,6-pentafluorophenyl sulfonamide

A solution of (E)-styrylsulfonyl chloride (10 mmol) and 2,3,4,5,6-pentafluoroaniline (10 mmol) was subjected to General Procedure 1, part B. The title compound, melting point 145–148° C., was obtained in 34.8% yield.

EXAMPLE 15

(E)-4-fluorostyryl-N-2,3,4,5,6-pentafluorophenyl sulfonamide

A solution of (E)-4-fluorostyrylsulfonyl chloride (10 mmol) and 2,3,4,5,6-pentafluoroaniline (10 mmol) was subjected to General Procedure 1, part B. The title compound, melting point 182–184° C., was obtained in 36.1% yield.

EXAMPLE 16

(E)-styryl-N-4-sulfamylphenyl sulfonamide

A solution of (E)-styrylsulfonyl chloride (10 mmol) and sulfanilamide (10 mmol) was subjected to General Procedure 1, part B. The title compound, melting point 171–173° C., was obtained in 80% yield.

EXAMPLE 17

(E)-4-methoxystyryl-N-4-sulfamylphenyl sulfonamide

A solution of (E)-4-methoxystyrylsulfonyl chloride (10 mmol) and sulfanilamide (10 mmol) was subjected to General Procedure 1, part B. The title compound, melting point 181–183° C., was obtained in 46.2% yield.

The following additional compounds, tabulated in Tables 5 and 6, are made by subjecting a solution containing a 10 mmolar concentration of the two indicated reactants to either General Procedure 1, part B (Examples Nos. 18, 19, 21–23, 26, 27, 30, 33, 36, 39, 41, 44, 47–50, 55, 59, 61, 64 and 65) or General Procedure 2, part D (Examples Nos. 20, 24, 25, 28, 29, 31, 32, 34, 35, 37, 38, 40, 42, 43, 45, 46, 51–54, 56–58, 60, 62, 63, 66 and 67).

TABLE 5

IV

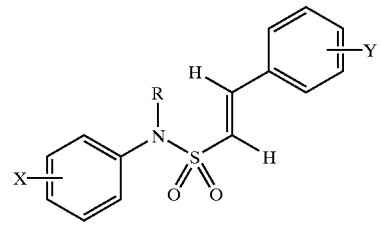

| Ex. | X | Y | Reactants | Product |
|---|---|---|---|---|
| 18 | 2-Cl | 2,3,4,5,6-F$_5$ | pentafluorostyrylsulfonyl chloride and 2-chloroaniline | (E)-pentafluorostyryl-N-2-chlorophenyl sulfonamide |
| 19 | 4-F | 2,3,4,5,6-F$_5$ | pentafluorostyrylsulfonyl chloride and 4-fluoroaniline sulfonamide | (E)-pentafluorostyryl-N-4-fluorophenyl sulfonamide |
| 20 | 4-Br | 2,3,4,5,6-F$_5$ | 4-bromophenylaminosulfonylacetic acid and pentafluorobenzaldehyde | (E)-pentafluorostyryl-N-4-bromophenyl sulfonamide |
| 21 | 2-F, 4-Cl | 2,3,4,5,6-F$_5$ | pentafluorostyrylsulfonyl chloride and 2-fluoro-4-chloroaniline | (E)-pentafluorostyryl-N-2-fluoro-4-chlorophenyl sulfonamide |
| 22 | 4-OCH$_3$ | 2,3,4,5,6-F$_5$ | pentafluorostyrylsulfonyl chloride and 4-methoxyaniline | (E)-pentafluorostyryl-N-4-methoxyphenyl sulfonamide |
| 23 | 3-F, 4-OCH$_3$ | 2,3,4,5,6-F$_5$ | pentafluorostyrylsulfonyl chloride and 3-fluoro-4-methoxyaniline | (E)-pentafluorostyryl-N-3-fluoro-4-methoxyphenyl sulfonamide |
| 24 | 2,3,4-(OCH$_3$)$_3$ | 2,3,4,5,6-F$_5$ | 2,3,4-trimethoxyphenylaminosulfonylacetic acid and pentafluorobenzaldehyde | (E)-pentafluorostyryl-N-2,3,4-trimethoxyphenyl sulfonamide |

TABLE 5-continued

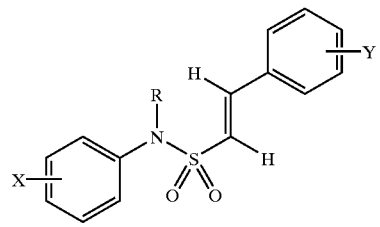

IV

| Ex. | X | Y | Reactants | Product |
|---|---|---|---|---|
| 25 | 4-OH | 2,3,4,5,6-$F_5$ | 4-hydroxyphenylaminosulfonylacetic acid and pentafluorobenzaldehyde | (E)-pentafluorostyryl-N-4-hydroxyphenyl sulfonamide |
| 26 | 4-$NO_2$ | 2,3,4,5,6-$F_5$ | pentafluorostyrylsulfonyl chloride and 4-nitroaniline | (E)-pentafluorostyryl-N-4-nitrophenyl sulfonamide |
| 27 | 4-$SO_2NH_2$ | 2,3,4,5,6-$F_5$ | pentafluorostyrylsulfonyl chloride and 4-sulfanilamide | (E)-pentafluorostyryl-N-4-sulfamylphenyl sulfonamide |
| 28 | 3-F, 4-$OCH_3$ | 2,3,4,5,6-$F_5$ | 3-fluoro-4-methoxyphenylaminosulfonylacetic acid and pentafluorobenzaldehyde | (E)-pentafluorostyryl-N-phenyl sulfonamide |
| 29 | 2,4,6-$(OCH_3)_3$ | 2,3,4,5,6-$F_5$ | 2,4,6-trimethoxyphenylaminosulfonylacetic acid and pentafluorobenzaldehyde | (E)-pentafluorostyryl-N-3-fluoro-4-methoxyphenyl sulfonamide |
| 30 | 2,3,4,5,6-$F_5$ | 2,3,4,5,6-$F_5$ | pentafluorostyrylsulfonyl chloride and pentafluoroaniline | (E)-pentafluorostyryl-N-pentafluorophenyl sulfonamide |
| 31 | 2-Cl | 2,4,6-$(OCH_3)_3$ | 2-chlorophenylaminosulfonylacetic acid and 2,4,6-trimethoxybenzaldehyde | (E)-2,4,6-trimethoxystyryl-N-2-chlorophenyl sulfonamide |
| 32 | 4-F | 2,4,6-$(OCH_3)_3$ | 4-bromophenylaminosulfonylacetic acid and 2,4,6-trimethoxybenzaldehyde | (E)-2,4,6-trimethoxystyryl-N-4-fluorophenyl sulfonamide |
| 33 | 4-Br | 2,4,6-$(OCH_3)_3$ | 2,4,6-trimethoxystyrylsulfonyl chloride and 4-bromoaniline | (E)-2,4,6-trimethoxystyryl-N-4-bromophenyl sulfonamide |
| 34 | 2-F, 4-Cl | 2,4,6-$(OCH_3)_3$ | 2-fluoro-4-chlorophenylaminosulfonylacetic acid and 2,4,6-trimethoxybenzaldehyde | (E)-2,4,6-trimethoxystyryl-N-2-fluoro-4-chlorophenyl sulfonamide |
| 35 | 4-$OCH_3$ | 2,4,6-$(OCH_3)_3$ | 4-methoxyphenylaminosulfonylacetic acid and 2,4,6-trimethoxybenzaldehyde | (E)-2,4,6-trimethoxystyryl-N-4-methoxyphenyl sulfonamide |
| 36 | 3-F, 4-$OCH_3$ | 2,4,6-$(OCH_3)_3$ | 2,4,6-trimethoxystyrylsulfonyl chloride and 3-fluoro-4-methoxyaniline | (E)-2,4,6-trimethoxystyryl-N-3-fluoro-4-methoxyphenyl sulfonamide |
| 37 | 2,3,4-$(OCH_3)_3$ | 2,4,6-$(OCH_3)_3$ | 2,3,4-trimethoxyphenylaminosulfonylacetic acid and 2,4,6-trimethoxybenzaldehyde | (E)-2,4,6-trimethoxystyryl-N-2,3,4-trimethoxyphenyl sulfonamide |
| 38 | 4-OH | 2,4,6-$(OCH_3)_3$ | 4-hydroxyphenylaminosulfonylacetic acid and 2,4,6-trimethoxybenzaldehyde | (E)-2,4,6-trimethoxystyryl-N-4-hydroxyphenyl sulfonamide |
| 39 | 4-$H_2PO_4$ | 2,4,6-$(OCH_3)_3$ | 2,4,6-trimethoxystyrylsulfonyl chloride and 4-phosphonatoaniline | (E)-2,4,6-trimethoxystyryl-N-4-phosphonatophenyl sulfonamide |
| 40 | 4-$NO_2$ | 2,4,6-$(OCH_3)_3$ | 4-nitrophenylaminosulfonylacetic acid and 2,4,6-trimethoxybenzaldehyde | (E)-2,4,6-trimethoxystyryl-N-4-nitrophenyl sulfonamide |
| 41 | 2,4,6-$(OCH_3)_3$ | 2,4,6-$(OCH_3)_3$ | 2,4,6-trimethoxystyrylsulfonyl chloride and 2,4,6-trimethoxyaniline | (E)-2,4,6-trimethoxystyryl-N-2,4,6-trimethoxyphenyl sulfonamide |
| 42 | 2,3,4,5,6-$F_5$ | 2,4,6-$(OCH_3)_3$ | 2,3,4,5,6-pentafluorophenylaminosulfonylacetic acid and 2,4,6-trimethoxybenzaldehyde | (E)-2,4,6-trimethoxystyryl-N-pentafluorophenyl sulfonamide |
| 43 | 4-$SO_2NH_2$ | 2,4,6-$(OCH_3)_3$ | 4-sulfamylphenylaminosulfonylacetic acid and 2,4,6-trimethoxybenzaldehyde | (E)-2,4,6-trimethoxystyryl-N-4-sulfamylphenyl sulfonamide |
| 44 | 2,3,4,5,6-$F_5$ | 2,4,6-$(OCH_3)_3$ | 2,4,6-trimethoxystyrylsulfonyl chloride and pentafluoroaniline | (E)-2,4,6-trimethoxystyryl-N-pentafluoro sulfonamide |
| 45 | 4-$OCH_3$ | 3,4,5-$(OCH_3)_3$ | 4-methoxyphenylaminosulfonylacetic acid and 3,4,5-trimethoxybenzaldehyde | (E)-3,4,5-trimethoxystyryl-N-4-methoxyphenyl sulfonamide |
| 46 | 3-F, 4-$OCH_3$ | 3,4,5-$(OCH_3)_3$ | 3-fluoro-4-methoxyphenylaminosulfonylacetic acid and 3,4,5-trimethoxybenzaldehyde | (E)-3,4,5-trimethoxystyryl-N-3-fluoro-4-methoxyphenyl sulfonamide |

TABLE 5-continued

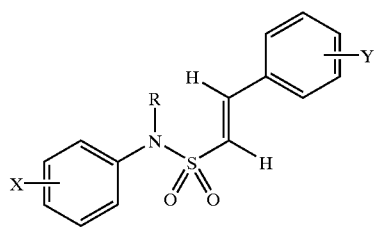

IV

| Ex. | X | Y | Reactants | Product |
|---|---|---|---|---|
| 47 | 2,3,4-(OCH$_3$)$_3$ | 3,4,5-(OCH$_3$)$_3$ | 3,4,5-trimethoxystyrylsulfonyl chloride and 2,3,4-trimethoxyaniline | (E)-3,4,5-trimethoxystyryl-N-2,3,4-trimethoxyphenyl sulfonamide |

TABLE 6

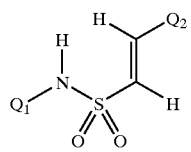

| Ex. | Q$_1$ | Q$_2$ | Reactants | Product |
|---|---|---|---|---|
| 48 | 2-benzothiazolyl | pentafluorophenyl | pentafluorostyryl-sulfonyl chloride and 2-aminobenzathiazole | (E)-pentafluorostyryl-N-3-benzothiazolylsulfonamide |
| 49 | 2-benzoxazolyl | 2,4,6-trimethoxyphenyl | 2,4,6-trimethoxystyrylsulfonyl chloride and 2-aminobenzoxazole | (E)-2,4,6-trimethoxystyryl-N-3-benzoxazolylsulfonamide |
| 50 | 2-thiazolyl | 4-methoxyphenyl | 4-methoxystyrylsulfonyl chloride and 2-aminothiazole | (E)-4-methoxystyryl-N-3-2-thiazolylsulfonamide |
| 51 | 3-indolyl | pentafluorophenyl | 3-indolylaminosulfonylacetic acid and pentafluorobenzaldehyde | (E)-pentafluorostyryl-N-3-indolyl sulfonamide |
| 52 | 4-indolyl | 2,4,6-trimethoxyphenyl | 4-indolylaminosulfonylacetic acid and 2,4,6-trimethoxybenzaldehyde | (E)-2,4,6-trimethoxystyryl-N-4-indolyl sulfonamide |
| 53 | 5-indolyl | 3-fluoro-4-methoxyphenyl | 5-indolylaminosulfonylacetic acid and 3-fluoro-4-methoxybenzaldehyde | (E)-3-fluoro-4-methoxystyryl-N-5-indolyl sulfonamide |
| 54 | 3-isoxazolyl | 3-indolyl | 3-isoxazolylaminosulfonylacetic acid and 3-indolylcarbaldehyde | (E)-N-3-isoxazolyl-3-indolyl ethenesulfonamide |
| 55 | 3-quinolinyl | 4-pyridinyl | 3-Aminoquinoline and 4-pyridine ethenyl sulfonylchloride | (E)-N-3-quinolinyl-4-pyridyl ethenesulfonamide |
| 56 | 3-(1,2,3-triazolyl) | pentafluorophenyl | 3-(1,2,3-triazolyl)aminosulfonylacetic acid and pentafluorobenzaldehyde | (E)-N-1,2,3-triazolyl-2,3,4,5,6-pentafluorostyrylsulfonamide |
| 57 | 2,4,6-trimethoxyphenyl | 5-indolyl | 2,4,6-trimethoxyphenylaminosulfonyl-acetic acid and 5-indolylcarboxaldehyde | (E)-N-2,4,6-trimethoxyphenyl-5-indolyl ethenesulfonamide |
| 58 | 2-imidazolyl | pentafluorophenyl | 2-imidazolylaminosulfonylacetic acid and pentafluorobenzaldehyde | (E)-N-2-imidazolyl-2,3,4,5,6-pentafluorostyrylsulfonamide |
| 59 | 5-isothiazolyl | 2-pyridinyl | 5-aminoisothiazole and 2-pyridene ethenyl sulfonylchloride | (E)-N-5-thiazolyl-2-pyridyl ethenesulfonamide |
| 60 | 3-pyrazolyl | 2,4,6-trimethoxyphenyl | 3-pyrazolylaminosulfonylacetic acid and 2,4,6-trimethoxybenzaldehyde | (E)-N-3-pyrazolyl-2,4,6-trimethoxystyryl sulfonamide |
| 61 | 4-cyano-3-pyrazolyl | pentafluorophenyl | 4-cyano-3-pyrazolylaminosulfonylacetic acid and pentafluorobenzaldehyde | (E)-N-4-cyano-3-pyrazolyl-pentafluorostyrylsulfonamide |
| 62 | 4-methoxyphenyl | 3-quinolinyl | 4-methoxyphenylaminosulfonylacetic acid and 3-quinolinylcarboxaldehyde | (E)-N-4-methoxyphenyl-3-quinolinyl ethenesulfonamide |
| 63 | 3-fluoro-4-methoxyphenyl | 5-indolyl | 3-fluoro-4-methoxyphenylaminosulfonyl-acetic acid and 5-indolylcarboxaldehyde | (E)-N-3-fluoro-4-methoxyphenyl-5-indolyl ethenesulfonamide |
| 64 | 2,3,4-trimethoxyphenyl | 3-pyrazolyl | 2,3,4-trimethoxyphenylaminosulfonyl-acetic acid and 3-pyrazolecarboxaldehyde | (E)-N-2,3,4-trimethoxyphenyl-3-pyrazolyl ethenesulfonamide |
| 65 | 4-hydroxyphenyl | 4-pyridinyl | 4-hydroxyaniline and 4-pyridine ethenyl sulfonylchloride | (E)-N-4-hydroxyphenyl-4-pyridyl ethenesulfonamide |
| 66 | pentafluorophenyl | 4-quinolinyl | pentafluorophenylaminosulfonylacetic acid and 4-quinolinylcarboxaldehyde | (E)-N-pentafluorophenyl-4-quinolinyl ethenesulfonamide |
| 67 | 2,4,6-trimethoxyphenyl | 2-imidazolyl | 2,4,6-trimethoxyphenylaminosulfonyl-acetic acid and 2-imidazolylcarboxaldehyde | (E)-N-2,4,6-trimethoxyphenyl-2-imidazolyl ethenesulfonamide |

EXAMPLE 68

Effect of N-(Aryl)-2-Arylethenesulfonamides on Tumor Cell Lines

The effect of the N-(aryl)-2-arylethenesulfonamides on normal fibroblasts and on tumor cells was determined by the assay described by Latham et al, Oncogene 12:827–837 (1996). Normal diploid lung human fibroblasts (HFL-1) or tumor cells (prostate, colorectal, breast, glial, pancreatic ovarian or leukemic) were plated in 6-well dishes at a cell density of $1.0 \times 10^5$ cells per 35-mm² well. The plated cells were treated 24 hours later with various concentrations of N-(aryl)-2-arylethenesulfonamide dissolved in dimethyl sulfoxide (DMSO). The total number of viable cells was determined 96 hours later by trypsinizing the wells and counting the number of viable cells, as determined by trypan blue exclusion, using a hemacytometer. Each compound tested (Exs. 1–17) inhibited cell proliferation when tested at a concentration of 30 micromolar. Some compounds inhibited proliferation at lower concentrations. Certain compounds induced cell death, at concentrations from 1 to 10 micromolar. Normal HFL cells were treated with the same compounds under the same conditions of concentration and time. The normal cells displayed growth inhibition but no appreciable cell death.

EXAMPLE 69

Determination of $GI_{50}$

A dose response curve was plotted for the tumor growth inhibitory effect of (E)-4-methoxystyryl-N-4-fluorophenyl sulfonamide on the estrogen-unresponsive breast cell line BT-20 (FIG. 1). The $GI_{50}$ (the concentration of drug resulting in 50% net loss of growth inhibition) was determined as 10 μM. In contrast, the normal fibroblast line HFL-1 exhibited a $GI_{50}$ of 50 μM. The (E)-4-methoxystyryl-N-4-fluorophenyl sulfonamide $GI_{50}$ for the same compound against the cell lines listed in Table 7 was determined in the same manner.

TABLE 7

$GI_{50}$ for growth inhibition effect of (E)-4-methoxystyryl-N-4-fluorophenyl sulfonamide on various cell lines

| CELL LINE | TUMOR TYPE | $GI_{50}$ (μM) |
| --- | --- | --- |
| DU145 | Prostate | 10 |
| PC-3 | Prostate | 20 |
| LNCAP | Prostate | 20 |
| DLD-1 | Colo-rectal | 15 |
| HCT-116 | Colo-rectal | 20 |
| COLO-320 | Colo-rectal | 5 |
| BT2O | Breast | 10 |
| SK-br-3 | Breast | 30 |
| U87 | Glioblastoma | 20 |
| MIA-PaCa-2 | Pancreatic | 7 |
| SK-ov-3 | Ovarian | 15 |
| CEM | Leukemic | 30 |
| HFL-1 | Normal diploid lung | 50 |

The $GI_{50}$ of (E)-4-methoxystyryl-N-3-fluoro-4-methoxyphenyl sulfonamide was determined for the following cell lines: BT20, DU145, H157 and DLD-1. The $GI_{50}$ for each cell line was in essential agreement with the $GI_{50}$ determined for (E)-4-methoxystyryl-N-4-fluorophenyl sulfonamide in the same cell line.

EXAMPLE 70

Induction of Apoptosis in Tumor Cells

The following assay demonstrates the apoptotic activity of the compounds of the invention against tumor cells.

Figure 2:
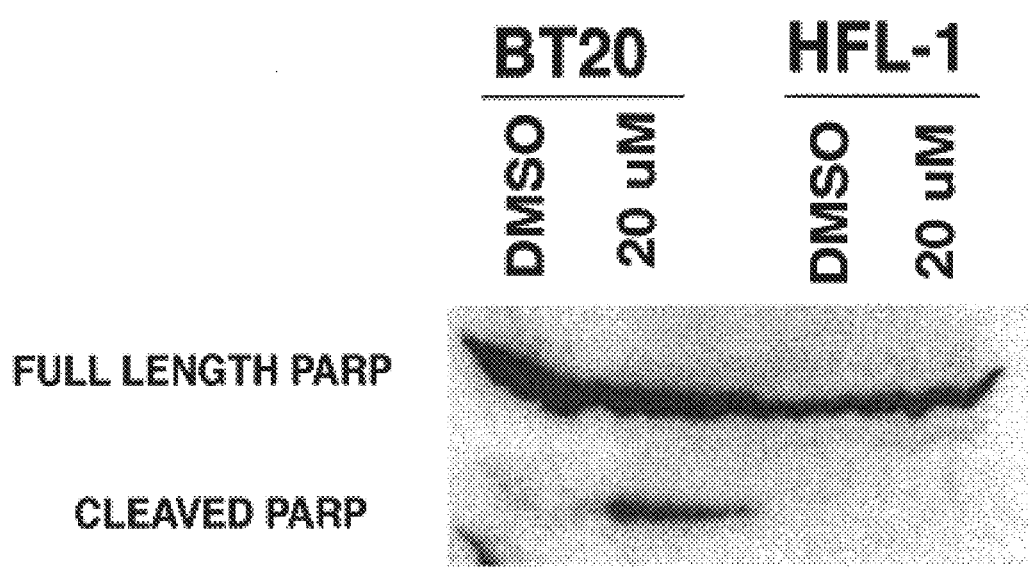
FIG. 2 is a Western blot of BT20 cells and normal human lung fibroblast cells (HFL-1) treated with 20 micromolar (E)-4-methoxystyryl-N-4-fluorophenyl sulfonamide or vehicle (DMSO) and probed with antibody which recognizes both full length and cleaved poly(ADP-ribose) polymerase (PARP). The 83 kDa cleavage product is a marker for apoptosis.

The caspases and the ICE-family proteases are cysteine proteases which are activated during apoptosis (Patel et al., FASEB 10:587–597, 1996). The cleavage of poly(ADP-ribose) polymerase (PARP), which is a target of caspase-3, apopain, and several other activated proteases, is a widely used and accepted marker for apoptosis (Nicholson et al., Nature 376(6533):37–43, 1995; Lippke et al., J. Biol. Chemistry 271:1825, 1996). For this assay, BT20 cells, an estrogen receptor negative breast carcinoma, and HFL-1 cells, normal lung fibroblasts, were treated with either (E)-4-methoxystyryl-N-4-fluorophenyl sulfonamide at a final concentration of 20 μM or dimethyl sulfoxide (DMSO) for 96 hours. The cells were then lysed in RIPA buffer and 100 μg of total cellular protein from each sample was resolved on a 10% SDS-polyacrylamide gel. The proteins were then Western blotted onto PROTRAN filter paper (S/S) and the filter was then probed with antibody (Boehringer Mannheim) specific for PARP. This antibody recognizes both the 116 kDa full length PARP and the 83 kDa cleaved product. The results, set forth in FIG. 2, show that a 96 hour treatment with the test compound specifically activated caspases in the treated breast carcinoma cell line and not in the normal cell line. The western blot clearly shows that only the test compound-treated BT20 cells had the presence of the 83 kDa PARP cleavage product. The HFL-1 cells treated in a similar manner showed no cleavage of the full length PARP. The BT20 cells treated with DMSO for the same amount of time also had no activation of the apoptotic pathway. These results show that the compounds of the invention selectively kill cancer cells by activating the apoptotic pathway as indicated by the activation of the cysteine proteases, a molecular marker for apoptosis. Cells which are not tumorigenic do not undergo apoptosis but become growth arrested at concentrations significantly higher than the concentration necessary for tumor cell death.

EXAMPLE 71

Radioprotective Effects of N-Aryl-2-Arylethenesulfonamides on Cultured Normal Cells The radioprotective effects of (a) styryl-N-phenylsulfonamide, (b) 4-methoxystyryl-N-flourophenylsulfonamide; (c) styryl-N-methyl-N-phenyl-sulfonamide and (d) 4-methoxystyryl-N-2,4,6-trimethoxyphenylsulfonamide were evaluated on cultured normal cells as follows.

HFL-1 cells, which are normal diploid lung fibroblasts, were plated into 24 well dishes at a cell density of 3000 cells per 10 mm² in DMEM completed with 10% fetal bovine serum and antibiotics. The test compounds were added to the cells 24 hours later in select concentrations from 2.5 μM and 10.0 μM, inclusive, using DMSO as a solvent. Control cells were treated with DMSO alone. The cells were exposed to the test compound or DMSO for 24 hours.

The cells were then irradiated with 10 Gy (gray) of ionizing radiation (IR) using a J. L. Shepherd Mark I, Model 30-1 Irradiator equipped with $^{137}$cesium as a source. After irradiation, the medium on the test and control cells was removed and replaced with fresh growth medium without the test compounds or DMSO. The irradiated cells were incubated for 96 hours and then duplicate wells were trypsinized and replated onto 100 mm² tissue culture dishes. The replated cells were grown under normal conditions with one change of fresh medium for 2 weeks. The number of colonies from each 100 mm² culture dish, which represents the number of surviving cells, was determined by staining the dishes as described below.

In order to visualize and count the colonies derived from the clonal outgrowth of individual protected cells, the medium was removed and the plates were washed one time with room temperature phosphate buffered saline. The cells were stained with a 1:10 diluted Modified Geimsa staining solution (Sigma) for 20 minutes. The stain was removed, and the plates were washed with tap water. The plates were air dried, the number of colonies from each plate was counted and the average from duplicate plates was determined. Each compound provided radioprotective activity of between 4- and 6-fold at the concentrations tested. Fold protection was determined by dividing the average number of colonies from the test plates by the average number of colonies counted on the control plates.

EXAMPLE 72

Protection of Mice from Radiation Toxicity by Pre-Treatment with N-Aryl-2-Arylethenesulfonamides C57 black mice age 10–12 weeks (Taconic) are divided into treatment groups of 10 mice each and given intraperitoneal injections of 200 micrograms of N-aryl-2-arylethenesulfonamide dissolved in DMSO (a 10 mg/Kg dose, based on 20 g mice). The injections are given 18 and 6 hours before irradiation with 8 Gy gamma radiation. A control group of 10 animals receives 8 Gy gamma radiation alone. Mortality of control and experimental groups is assessed for 40 days after irradiation.

EXAMPLE 73

Radioprotective Effect of N-Aryl-2-Arylethenesulfonamides in Mice When Given After Radiation Exposure C57 B6/J mice age 10–12 weeks (Taconic) are divided into treatment groups and one control group of 10 mice each. Each treatment group receives intraperitoneal injections of 200 micrograms of N-aryl-2-arylethenesulfonamide dissolved in DMSO (a 10 mg/Kg dose, based on 20 g mice) 15 minutes after irradiation with 8 Gy gamma radiation. The control group receives 8 Gy gamma radiation alone. Mortality of control and treatment groups are assessed for 40 days after irradiation.

EXAMPLE 74

Effect of Exposure to Ionizing Radiation on Normal and Malignant Hematopoietic Progenitor Cell Growth After Pretreatment with N-Aryl-2-Arylethenesulfonamides The effect of ionizing radiation on normal and malignant hematopoietic progenitor cells which are pretreated with N-aryl-2-arylethenesulfonamides is investigated by assessing cloning efficiency and development of the pretreated cells after irradiation.

To obtain hematopoietic progenitor cells, human bone marrow cells (BMC) or peripheral blood cells (PB) are obtained from normal healthy, or acute or chronic myelogenous leukemia (AML, CML), volunteers by Ficoll-Hypaque density gradient centrifugation, and are partially enriched for hematopoietic progenitor cells by positively selecting CD34$^+$ cells with immunomagnetic beads (Dynal A. S., Oslo, Norway). The CD34$^+$ cells are suspended in supplemented alpha medium and incubated with mouse anti-HPCA-I antibody in 1:20 dilution, 45 minutes, at 4° C. with gentle inverting of tubes. Cells are washed x3 in supplemented alpha medium, and then incubated with beads coated with the Fc fragment of goat anti-mouse IgG$_1$ (75 µl of immunobeads/ 10$^7$ CD34$^+$ cells). After 45 minutes of incubation (4° C.), cells adherent to the beads are positively selected using a magnetic particle concentrator as directed by the manufacturer.

2x10$^4$ CD34$^+$ cells are incubated in 5 ml polypropylene tubes (Fisher Scientific, Pittsburgh, Pa.) in a total volume of 0.4 ml of Iscove's modified Dulbecco's medium (IMDM) containing 2% human AB serum and 10 mM Hepes buffer. An N-aryl-2-arylethenesulfonamide, for example styryl-N-phenylsulfonamide; 4-methoxystyryl-N-flourophenylsulfonamide; styryl-N-methyl-N-phenylsulfonamide; or 4-methoxystyryl-N-2,4,6-trimethoxyphenyl-sulfonamide at three different concentrations (2.5 µM, 5.0 µM and 10.0 µM) in DMSO are added separately to the cells. Control cells received DMSO alone. The cells are incubated for 20–24 hours and irradiated with 5 Gy or 10 Gy of ionizing radiation. Immediately after irradiation, the medium is removed and replaced with fresh medium without the test compound or DMSO. Twenty-four hours after irradiation, the treatment and control cells are prepared for plating in plasma clot or methylcellulose cultures. Cells (1x10$^4$ CD34$^+$ cells per dish) were not washed before plating.

Assessment of the cloning efficiency and development of the treated hematopoietic progenitor cells are carried out essentially as reported in Gewirtz et al., Science 242, 1303–1306 (1988), the disclosure of which is incorporated herein by reference.

EXAMPLE 75

Bone Marrow Purging with Ionizing Radiation After Pretreatment with N-Aryl-2-Arylethenesulfonamides Bone marrow is harvested from the iliac bones of a subject under general anesthesia in an operating room using standard techniques. Multiple aspirations are taken into heparinized syringes. Sufficient marrow is withdrawn so that the subject will be able to receive about 4x10$^8$ to about 8x10$^8$ processed marrow cells per kg of body weight. Thus, about 750 to 1000 ml of marrow is withdrawn. The aspirated marrow is transferred immediately into a transport medium (TC-199, Gibco, Grand Island, N.Y.) containing 10,000 units of preservative-free heparin per 100 ml of medium. The aspirated marrow is filtered through three progressively finer meshes to obtain a cell suspension devoid of cellular aggregates, debris and bone particles. The filtered marrow is then processed further into an automated cell separator (e.g., Cobe 2991 Cell Processor) which prepares a "buffy coat" product, (i.e., leukocytes devoid of red cells and platelets). The buffy coat preparation is then placed in a transfer pack for further processing and storage. It may be stored until purging in liquid nitrogen using standard procedures. Alternatively, purging can be carried out immediately, then the purged marrow may be stored frozen in liquid nitrogen until it is ready for transplantation.

The purging procedure is carried out as follows. Cells in the buffy coat preparation are adjusted to a cell concentration of about 2x10$^7$/ml in TC-199 containing about 20% autologous plasma. An N-aryl-2-arylethenesulfonamide; for example 2.5 to 10 micromolar of either styryl-N-phenylsulfonamide; 4-methoxystyryl-N-flourophenylsulfonamide; styryl-N-methyl-N-phenylsulfonamide; or 4-methoxystyryl-N-2,4,6- trimethoxyphenylsulfonamide in DMSO is added to the transfer packs containing the cell suspension and incubated in a 37° C. water bath for 20–24 hours with gentle shaking. The transfer packs are then exposed to 5–10 Gy ionizing radiation. Recombinant human hematopoietic growth factors, e.g., rH IL-3 or rH GM-CSF, may be added to the suspension to stimulate growth of hematopoietic neoplasms and thereby increase their sensitivity to ionizing radiation.

The cells may then either be frozen in liquid nitrogen or washed once at 4° C. in TC-199 containing about 20% autologous plasma. Washed cells are then infused into the subject. Care must be taken to work under sterile conditions wherever possible and to maintain scrupulous aseptic techniques at all times.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A compound of the formula:

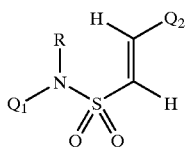

I wherein:
Q$_1$ and Q$_2$ are independently selected from the group consisting of substituted and unsubstituted aryl, and substituted and unsubstituted heteroaryl;
R is selected from the group consisting of hydrogen, (C$_1$–C$_6$)alkyl, (C$_1$–C$_6$)alkoxy, (C$_3$–C$_6$)alkenyl, (C$_2$–C$_6$)heteroalkyl, (C$_3$–C$_6$)heteroalkenyl, (C$_2$–C$_6$) hydroxyalkyl, substituted aryl, unsubstituted aryl, substituted heteroaryl, unsubstituted heteroaryl, substituted aryl(C$_1$–C$_3$)alkyl, unsubstituted aryl(C$_1$–C$_3$) alkyl, substituted heteroaryl(C$_1$–C$_3$)alkyl and unsubstituted heteroaryl(C$_1$–C$_3$)alkyl;
wherein the substituents for the substituted aryl and substituted heteroaryl groups comprising Q$_1$ are independently selected from the group consisting of halogen, (C$_1$–C$_6$)alkyl, (C$_1$–C$_6$)alkoxy, nitro, cyano, carboxy, carboxy(C$_1$–C$_3$)alkoxy, hydroxy, (C$_2$–C$_6$) hydroxyalkyl, phosphonato, amino, (C$_1$–C$_6$)acylamino, sulfamyl, acetoxy, di(C$_1$–C$_6$)alkylamino(C$_2$–C$_6$) alkoxy, trifluoromethyl and

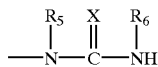

wherein:
X is oxygen or sulfur,
R$^5$ is selected from the group consisting of hydrogen, (C$_1$–C$_6$)alkyl, (C$_2$–C$_6$)heteroalkyl, substituted phenyl, and unsubstituted phenyl, and
R$^6$ is selected from the group consisting of hydrogen, (C$_1$–C$_6$)alkyl, (C$_2$–C$_6$)heteroalkyl, substituted aryl, unsubstituted aryl, substituted heteroaryl, unsubstituted heteroaryl, substituted aryl(C$_1$–C$_3$)alkyl, unsubstituted aryl-(C$_1$–C$_3$)alkyl and (C$_1$–C$_6$) alkoxycarbonyl(C$_1$–C$_6$)alkylenyl;

wherein the substituents for the substituted aryl and substituted heteroaryl groups comprising Q$_2$, and the substituents for the substituted aryl and substituted heteroaryl groups comprising or included with R, R$^5$ and R$^6$, are independently selected from the group consisting of halogen, (C$_1$–C$_6$)alkyl, (C$_1$–C$_6$)alkoxy, nitro, cyano, carboxy, carboxy(C$_1$–C$_3$)alkoxy, hydroxy, (C$_2$–C$_6$)hydroxyalkyl, phosphonato, amino, (C$_1$–C$_6$) acylamino, sulfamyl, acetoxy, di(C$_1$–C$_6$)alkylamino (C$_2$–C$_6$) and trifluoromethyl;

provided, that when R is hydrogen:
(a) when Q$_1$ is unsubstituted phenyl, Q$_2$ is other than dimethoxyphenyl, 2-methylphenyl, 2-chlorophenyl, 4-chlorophenyl, 4-N,N-dimethylaminophenyl, 4-methylphenyl, 4-methoxyphenyl, 4-nitrophenyl, 3-methoxy-4-hydroxyphenyl, unsubstituted phenyl, unsubstituted phenyl, unsubstituted benzodioxyolyl, unsubstituted 1-naphthyl and unsubstituted 2-thienyl;
(b) when Q$_1$ is 2,4-dinitrophenyl, Q$_2$ is other than 4-methylphenyl, 4-methoxyphenyl, 4-nitrophenyl, 4-bromophenyl, 3,4-dichlorophenyl, unsubstituted phenyl or unsubstituted 1-naphthyl;
(c) when Q$_1$ is 3-hydroxyphenyl, Q$_2$ is other than nitrophenyl;
(d) when Q$_1$ is 2-methyl-5-hydroxyphenyl, Q$_2$ is other than 4-nitrophenyl;
(e) when Q$_1$ is unsubstituted 2-pyridyl, Q$_2$ is other than 3-methoxy-4-hydroxyphenyl; and
(f) when Q$_2$ is unsubstituted phenyl, Q$_1$ is other than 2-hydroxyphenyl, 2-aminophenyl, 3,4-dichlorophenyl or unsubstituted 2-pyridil;

or a pharmaceutically acceptable salt thereof.

2. A compound according to claim 1, provided:
(a) when Q$_1$ is unsubstituted phenyl, Q$_2$ is other than dialkoxyphenyl, 2-alkylphenyl, 2-halophenyl, 4-halophenyl, 4-N,N-dialkylaminophenyl, 4-alkylphenyl, 4-alkoxyphenyl, 4-nitrophenyl, 3-alkoxy-4-hydroxyphenyl, unsubstituted phenyl, unsubstituted phenyl, unsubstituted benzodioxyolyl, unsubstituted 1-naphthyl and unsubstituted 2-thienyl;
when Q$_1$ is 2,4-dinitrophenyl, Q$_2$ is other than 4alkylphenyl, 4-alkoxyphenyl, 4-nitrophenyl, 4-halophenyl, 3,4-dihalophenyl, unsubstituted phenyl or unsubstituted 1naphthyl;
(c) when Q$_1$ is 2-methyl-5-hydroxyphenyl, Q$_2$ is other than 4-nitrophenyl;
(d) when Q$_1$ is unsubstituted 2-pyridyl, Q$_2$ is other than 3-methoxy-4-hydroxyphenyl; and
(e) when Q$_2$ is unsubstituted phenyl, Q$_1$ is other than 2-hydroxyphenyl, 2-aminophenyl, 3,4-dihalophenyl or unsubstituted 2-pyridyl;

or a pharmaceutically acceptable salt thereof.

3. A compound according to claim 2, provided:
when R is hydrogen:
(i) Q$_1$ may not be dinitrophenyl;
(ii) Q$_2$ may not be dinitrophenyl; and
(iii) when Q$_2$ is mononitrophenyl:
Q$_1$ is other than substituted phenyl, or
Q$_1$ is substituted phenyl wherein at least the 4-position is substituted, and the substituent is other than hydroxy;

or a pharmaceutically acceptable salt thereof.

4. A compound according to claim 1 wherein R is hydrogen or (C$_1$–C$_6$)alkyl.

5. A compound according to claim 4 wherein Q$_1$ and Q$_2$ are optionally substituted phenyl.

6. A compound according to claim 5 wherein at least one of $Q_1$ and $Q_2$ is substituted in at least the 4-position.

7. A compound according to claim 6 wherein the substituents are independently selected from the group consisting of halogen, $(C_1$–$C_6)$alkyl, $(C_1$–$C_6)$alkoxy, nitro, hydroxy and sulfamyl.

8. A compound according to claim 7 wherein the compound is (E)-styryl-N-4-sulfamylphenyl sulfonamide, or a pharmaceutically acceptable salt thereof.

9. A compound according to claim 7 wherein the compound is (E)-styryl-N-4-chlorophenyl sulfonamide or (E)-styryl-N-4-fluorophenyl sulfonamide, or a pharmaceutically acceptable salt thereof.

10. A compound according to claim 7 wherein the compound is (E)-4-methoxystyryl-N-methyl-N-phenyl sulfonamide, or a pharmaceutically acceptable salt thereof.

11. A compound according to claim 7 wherein the compound is (E)-4-chlorostyryl-N-3-chlorophenyl sulfonamide, or a pharmaceutically acceptable salt thereof.

12. A compound according to claim 7 wherein the compound is (E)-4-chlorostyryl-N-2-chlorophenyl sulfonamide, or a pharmaceutically acceptable salt thereof.

13. A compound according to claim 6 wherein $Q_1$ and $Q_2$ are both independently substituted in at least the 4-position.

14. A compound according to claim 13 wherein the substituents are independently selected from the group consisting of halogen, $(C_1$–$C_6)$ alkyl, $(C_1$–$C_6)$alkoxy, nitro, hydroxy and sulfamyl.

15. A compound according to claim 14 wherein the compound is (E)-4-methoxystyryl-N-4-sulfamylphenyl sulfonamide, or a pharmaceutically acceptable salt thereof.

16. A compound according to claim 14 wherein the compound is (E)-4-chlorostyryl-N-3-fluoro-4-methoxyphenyl sulfonamide, or a pharmaceutically acceptable salt thereof.

17. A compound according to claim 14 wherein the compound is (E)-4-chlorostyryl-N-4-fluorophenyl sulfonamide, or a pharmaceutically acceptable salt thereof.

18. A compound according to claim 14 wherein the compound is (E)-4-methoxystyryl-N-4-fluorophenyl sulfonamide, or a pharmaceutically acceptable salt thereof.

19. A compound according to claim 14 wherein the compound is (E)-4-methoxystyryl-N-3-fluoro-4-methoxyphenyl sulfonamide, or a pharmaceutically acceptable salt thereof.

20. A compound according to claim 14 wherein the compound is (E)-4-methoxystyryl-N-4-fluorophenyl sulfonamide, or a pharmaceutically acceptable salt thereof.

21. A compound according to claim 14 wherein the compound is (E)-4-fluorostyryl-N-4-chlorophenyl sulfonamide, or a pharmaceutically acceptable salt thereof.

22. A compound according to claim 14 wherein the compound is (E)-4-methoxystyryl-N-2,4,6-trimethoxyphenyl sulfonamide, or a pharmaceutically acceptable salt thereof.

23. A compound according to claim 6 of the formula:

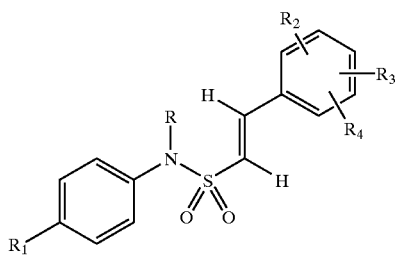

II wherein R is hydrogen or $(C_1$–$C_6)$alkyl; $R_1$ is selected from the group consisting of halogen, $(C_1$–$C_6)$alkyl, $(C_1$–$C_6)$alkoxy, nitro, cyano, carboxy, carboxy$(C_1$–$C_3)$alkoxy, hydroxy, $(C_2$–$C_6)$hydroxyalkyl, phosphonato, amino, $(C_1$–$C_6)$acylamino, sulfamyl, acetoxy, di$(C_1$–$C_6)$alkylamino $(C_2$–$C_6)$alkoxy and trifluoromethyl; and $R^2$, $R^3$ and $R^4$, are independently selected from the group consisting of $(C_1$–$C_6)$alkoxy.

24. A compound according to claim 23 of the formula:

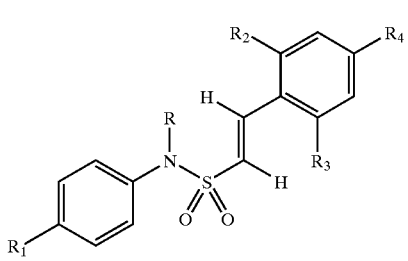

IIa wherein R, $R^1$, $R^2$, $R^3$ and $R^4$ are defined as in claim 23.

25. A compound according to claim 24, wherein the compound is (E)-2,4,6-trimethoxystyryl-N-4-methoxyphenyl sulfonamide, or a pharmaceutically acceptable salt thereof.

26. A compound according to claim 5 wherein at least one of $Q_1$ and $Q_2$ is pentasubstituted with halogen.

27. A compound according to claim 26 wherein at least one of $Q_1$ and $Q_2$ is pentafluorophenyl.

28. A compound according to claim 27 selected from the group consisting of (E)-4-methoxystyryl-N-2,3,4,5,6-pentafluorophenyl sulfonamide, (E)-styryl-N-2,3,4,5,6-pentafluorophenyl sulfonamide, (E)-4-fluorostyryl-N-2,3,4,5,6-pentafluorophenyl sulfonamide and pharmaceutically acceptable salts thereof.

29. A pharmaceutical composition comprising a pharmaceutically acceptable carrier at least one compound of the formula:

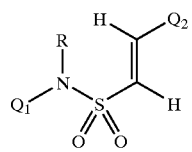

I wherein:
$Q_1$ and $Q_2$ are independently selected from the group consisting of substituted and unsubstituted aryl, and substituted and unsubstituted heteroaryl;
R is selected from the group consisting of hydrogen, $(C_1$–$C_6)$alkyl, $(C_1$–$C_6)$alkoxy, $(C_3$–$C_6)$alkenyl, ($C_2$–$C_6$)heteroalkyl, ($C_3$–$C_6$)heteroalkenyl, ($C_2$–$C_6$) hydroxyalkyl, substituted aryl, unsubstituted aryl, substituted heteroaryl, unsubstituted heteroaryl, substituted aryl($C_1$–$C_3$)alkyl, unsubstituted aryl($C_1$–$C_3$) alkyl, substituted heteroaryl($C_1$–$C_3$)alkyl and unsubstituted heteroaryl($C_1$–$C_3$)alkyl;

wherein the substituents for the substituted aryl and substituted heteroaryl groups comprising $Q_1$ are independently selected from the group consisting of halogen, ($C_1$–$C_6$)alkyl, ($C_1$–$C_6$)alkoxy, nitro, cyano, carboxy, carboxy($C_1$–$C_3$)alkoxy, hydroxy, ($C_2$–$C_6$) hydroxyalkyl, phosphonato, amino, ($C_1$–$C_6$)acylamino, sulfamyl, acetoxy, di($C_1$–$C_6$)alkylamino($C_2$–$C_6$) alkoxy), trifluoromethyl and

wherein:
X is oxygen or sulfur,
$R^5$ is selected from the group consisting of hydrogen, ($C_1$–$C_6$)alkyl, ($C_2$–$C_6$)heteroalkyl, substituted phenyl, and unsubstituted phenyl, and
$R^6$ is selected from the group consisting of hydrogen, ($C_1$–$C_6$)alkyl, ($C_2$–$C_6$)heteroalkyl, substituted aryl, unsubstituted aryl, substituted heteroaryl, unsubstituted heteroaryl, substituted aryl($C_1$–$C_3$)alkyl, unsubstituted aryl-($C_1$–$C_3$)alkyl and ($C_1$–$C_6$) alkoxycarbonyl($C_1$–$C_6$)alkylenyl;

wherein the substituents for the substituted aryl and substituted heteroaryl groups comprising $Q_2$, and the substituents for the substituted aryl and substituted heteroaryl groups comprising or included within R, $R^5$ and $R^6$, are independently selected from the group consisting of halogen, ($C_1$–$C_6$)alkyl, ($C_1$–$C_6$)alkoxy, nitro, cyano, carboxy, carboxy($C_1$–$C_3$)alkoxy, hydroxy, ($C_2$–$C_6$)hydroxyalkyl, phosphonato, amino, ($C_1$–$C_6$) acylamino, sulfamyl, acetoxy, di($C_1$–$C_6$)alkylamino ($C_2$–$C_6$ alkoxy) and trifluoromethyl;

provided, when R is hydrogen and $Q_2$ is unsubstituted phenyl, then $Q_1$ must be other than dihalophenyl;
or a pharmaceutically acceptable salt thereof.

30. A composition according to claim 29 wherein R is hydrogen or ($C_1$–$C_6$)alkyl.

31. A composition according to claim 30 wherein $Q_1$ and $Q_2$ are optionally substituted phenyl.

32. A composition according to claim 31 wherein at least one of $Q_1$ and $Q_2$ is substituted in at least the 4-position.

33. A composition according to claim 31 wherein the substituents are independently selected from the group consisting of halogen, ($C_1$–$C_6$)alkyl, ($C_1$–$C_6$)alkoxy nitro, hydroxy and sulfamyl.

34. A composition according to claim 33 wherein the compound is (E)-styryl-N-4-sulfamylphenyl sulfonamide, or a pharmaceutically acceptable salt thereof.

35. A composition according to claim 33 wherein the compound is (E)-styryl-N-4-chlorophenyl sulfonamide or E)-styryl-N-4-fluorophenyl sulfonamide, or a pharmaceutically acceptable salt thereof.

36. A composition according to claim 33 wherein the compound is (E)-4-methoxystyryl-N-methyl-N-phenyl sulfonamide, or a pharmaceutically acceptable salt thereof.

37. A composition according to claim 33 wherein the compound is (E)-4-chlorostyryl-N-3-chlorophenyl sulfonamide, or a pharmaceutically acceptable salt thereof.

38. A composition according to claim 33 wherein the compound is (E)-4-chlorostyryl-N-2-chlorophenyl sulfonamide, or a pharmaceutically acceptable salt thereof.

39. A composition according to claim 32 wherein $Q_1$ and $Q_2$ are both independently substituted in at least the 4-position.

40. A composition according to claim 39 wherein the substituents are independently selected from the group consisting of halogen, ($C_1$–$C_6$)alkyl, ($C_1$–$C_6$)alkoxy nitro, hydroxy and sulfamyl.

41. A composition according to claim 40 wherein the compound is (E)-4-methoxystyryl-N-4-sulfamylphenyl sulfonamide, or a pharmaceutically acceptable salt thereof.

42. A composition according to claim 40 wherein the compound is (E)-4-chlorostyryl-N-3-fluoro-4-methoxyphenyl sulfonamide, or a pharmaceutically acceptable salt thereof.

43. A composition according to claim 40 wherein the compound is (E)-4-chlorostyryl-N-4-fluorophenyl sulfonamide, or a pharmaceutically acceptable salt thereof.

44. A composition according to claim 40 wherein the compound is (E)-4-methoxystyryl-N-4-fluorophenyl sulfonamide, or a pharmaceutically acceptable salt thereof.

45. A composition according to claim 40 wherein the compound is (E)-4-methoxystyryl-N-3-fluoro-4-methoxyphenyl sulfonamide, or a pharmaceutically acceptable salt thereof.

46. A composition according to claim 40 wherein the compound is (E)-4-methoxystyryl-N-4-fluorophenyl sulfonamide, or a pharmaceutically acceptable salt thereof.

47. A composition according to claim 40 wherein the compound is (E)-4-fluorostyryl-N-4-chlorophenyl sulfonamide, or a pharmaceutically acceptable salt thereof.

48. A composition according to claim 40 wherein the compound is (E)-4-methoxystyryl-N-2,4,6-trimethoxyphenyl sulfonamide, or a pharmaceutically acceptable salt thereof.

49. A composition according to claim 40 wherein the at least one compound is a compound of the formula:

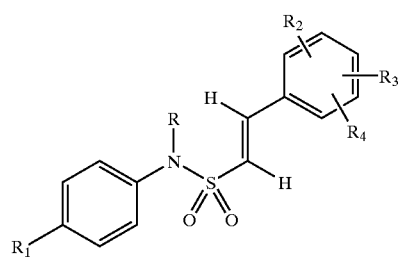

II wherein R is hydrogen or ($C_1$–$C_6$)alkyl, $R^1$ is selected from the group consisting of halogen, ($C_1$–$C_6$)alkyl, ($C_1$–$C_6$) alkoxy, nitro, cyano, carboxy, carboxy($C_1$–$C_3$)alkoxy, hydroxy, ($C_2$–$C_6$)hydroxyalkyl, phosphonato, amino, ($C_1$–$C_6$)acylamino, sulfamyl, acetoxy, di($C_1$–$C_6$)alkylamino ($C_2$–$C_6$)alkoxy, trifluoromethyl, and $R^2$, $R^3$ and $R^4$, are independently selected from the group consisting of ($C_1$–$C_6$) alkoxy.

50. A composition according to claim 49 wherein the at least one compound is a compound of the formula:

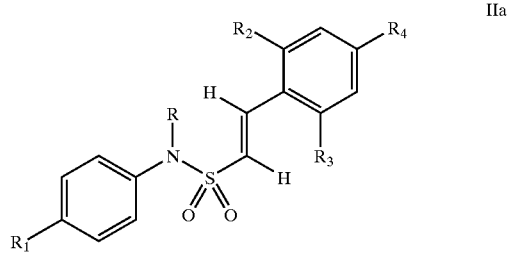

IIa wherein R, $R^1$, $R^2$, $R^3$ and $R^4$ are defined as in claim 49.

51. A composition according to claim 50 wherein the compound is (E)-2,4,6-trimethoxystyryl-N-4-methoxyphenyl sulfonamide, or a pharmaceutically acceptable salt thereof.

52. A composition according to claim 32 wherein at least one of $Q_1$ and $Q_2$ is pentasubstituted with halogen.

53. A composition according to claim 52 wherein at least one of $Q_1$ and $Q_2$ is pentafluorophenyl.

54. A method of treating an individual for a proliferative disorder comprising administering to said individual an effective amount of at least one compound of the formula:

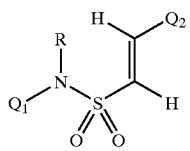

I wherein:
$Q_1$ and $Q_2$ are independently selected from the group consisting of substituted and unsubstituted aryl, and substituted and unsubstituted heteroaryl;
R is selected from the group consisting of hydrogen, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$hydroxyalkyl, substituted aryl, unsubstituted aryl, substituted heteroaryl, unsubstituted heteroaryl, substituted aryl$(C_1-C_3)$alkyl, unsubstituted aryl$(C_1-C_3)$alkyl, substituted heteroaryl$(C_1-C_3)$alkyl and unsubstituted heteroaryl$(C_1-C_3)$alkyl;
wherein the substituents for the substituted aryl and substituted heteroaryl groups comprising $Q_1$ are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$acylamino, sulfamyl, acetoxy, di$(C_1-C_6)$alkylamino$(C_2-C_6)$alkoxy, trifluoromethyl and

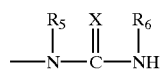

wherein:
X is oxygen or sulfur,
$R^5$ is selected from the group consisting of hydrogen, $(C_1-C_6)$alkyl, $(C_2-C_6)$heteroalkyl, substituted phenyl and unsubstituted phenyl, and
$R^6$ is selected from the group consisting of hydrogen, $(C_1-C_6)$alkyl, $(C_2-C_6)$heteroalkyl, substituted aryl, unsubstituted aryl, substituted heteroaryl, unsubstituted heteroaryl, substituted aryl$(C_1-C_3)$alkyl, unsubstituted aryl-$(C_1-C_3)$alkyl and $(C_1-C_6)$alkoxycarbonyl$(C_1-C_6)$alkylenyl;
wherein the substituents for the substituted aryl and substituted heteroaryl groups comprising $Q_2$, and the substituents for the substituted aryl and substituted heteroaryl groups comprising or included within R, $R^5$ and $R^6$, are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$acylamino, sulfamyl, acetoxy, di$(C_1-C_6)$alkylamino $(C_2-C_6$ alkoxy) and trifluoromethyl;
or a pharmaceutically acceptable salt thereof.

55. A method according to claim 54 wherein the proliferative disorder is selected from the group consisting of hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

56. A method according to claim 54 wherein the proliferative disorder is cancer.

57. A method of according to claim 56 wherein the cancer is selected from the group consisting of ovarian, breast, prostate, lung, renal, colorectal and brain cancers, or the cancer is a leukemia.

58. A method of inducing apoptosis of tumor cells in an individual afflicted with cancer comprising administering to said individual an effective amount of at least one compound of the formula:

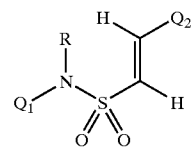

I wherein:
$Q_1$ and $Q_2$ are independently selected from the group consisting of substituted and unsubstituted aryl, and substituted and unsubstituted heteroaryl;
R is selected from the group consisting of hydrogen, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$hydroxyalkyl, substituted aryl, unsubstituted aryl, substituted heteroaryl, unsubstituted heteroaryl, substituted aryl$(C_1-C_3)$alkyl, unsubstituted aryl$(C_1-C_3)$alkyl, substituted heteroaryl$(C_1-C_3)$alkyl and unsubstituted heteroaryl$(C_1-C_3)$alkyl;
wherein the substituents for the substituted aryl and substituted heteroaryl groups comprising $Q_1$ are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$acylamino, sulfamyl, acetoxy, di(C1–C6)alkylamino$(C_2-C_6)$alkoxy, trifluoromethyl and

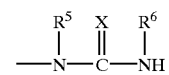

wherein:
X is oxygen or sulfur,
$R^5$ is selected from the group consisting of hydrogen, $(C_1-C_6)$alkyl, $(C_2-C_6)$heteroalkyl, substituted phenyl, and unsubstituted phenyl, and
$R^6$ is selected from the group consisting of hydrogen, $(C_1-C_6)$alkyl, $(C_2-C_6)$heteroalkyl, substituted aryl, unsubstituted aryl, substituted heteroaryl, unsubstituted heteroaryl, substituted aryl$(C_1-C_3)$alkyl, unsubstituted aryl-$(C_1-C_3)$alkyl and $(C_1-C_6)$alkoxycarbonyl$(C_1-C_6)$alkylenyl; and
wherein the substituents for the substituted aryl and substituted heteroaryl groups comprising $Q_2$, and the substituents for the substituted aryl and substituted heteroaryl groups comprising or included within R, $R^5$ and $R^6$, are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$ acylamino, sulfamyl, acetoxy, di$(C_1-C_6)$alkylamino $(C_2-C_6$ alkoxy$)$ and trifluoromethyl;

or a pharmaceutically acceptable salt thereof.

59. A method according to claim 58 wherein the tumor cells are selected from the group consisting of ovarian, breast, prostate, lung, colorectal, renal and brain tumors.

60. A method of reducing or eliminating the effects of ionizing radiation on normal cells in a subject who has incurred or is at risk for incurring exposure to ionizing radiation, comprising administering to the subject an effective amount of at least one radioprotective compound according to the following formula to the subject prior to or after exposure to ionizing radiation:

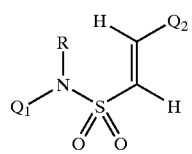

wherein:
$Q_1$ and $Q_2$ are independently selected from the group consisting of substituted and unsubstituted aryl, and substituted and unsubstituted heteroaryl;
R is selected from the group consisting of hydrogen, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$ hydroxyalkyl, substituted aryl, unsubstituted aryl, substituted heteroaryl, unsubstituted heteroaryl, substituted aryl$(C_1-C_3)$alkyl, unsubstituted aryl$(C_1-C_3)$ alkyl, substituted heteroaryl$(C_1-C_3)$alkyl and unsubstituted heteroaryl$(C_1-C_3)$alkyl;
wherein the substituents for the substituted aryl and substituted heteroaryl groups comprising $Q_1$ are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$ hydroxyalkyl, phosphonato, amino, $(C_1-C_6)$acylamino, sulfamyl, acetoxy, di$(C_1-C_6)$alkylamino$(C_2-C_6)$ alkoxy, trifluoromethyl and

wherein:
X is oxygen or sulfur,
$R^5$ is selected from the group consisting of hydrogen, $(C_1-C_6)$alkyl, $(C_2-C_6)$heteroalkyl, substituted phenyl and unsubstituted phenyl, and
$R^6$ is selected from the group consisting of hydrogen, $(C_1-C_6)$alkyl, $(C_2-C_6)$heteroalkyl, substituted aryl, unsubstituted aryl, substituted heteroaryl, unsubstituted heteroaryl, substituted aryl$(C_1-C3)$alkyl, unsubstituted aryl-$(C1-C3)$alkyl and $(C1-C_6)$ alkoxycarbonyl$(C_1-C_6)$alkylenyl;
wherein the substituents for the substituted aryl and substituted heteroaryl groups comprising $Q_2$, and the substituents for the substituted aryl and substituted heteroaryl groups comprising or included within R, $R^5$ and $R^6$, are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$ acylamino, sulfamyl, acetoxy, di$(C_1-C_6)$alkylamino $(C_2-C_6$ alkoxy$)$ and trifluoromethyl;

or a pharmaceutically acceptable salt thereof.

61. The method of claim 60, wherein the radioprotective compound is administered before exposure to the ionizing radiation.

62. The method of claim 61 wherein the radioprotective compound is administered at least about 6 hours before exposure to the ionizing radiation.

63. The method of to claim 62 wherein the radioprotective compound is administered no more than about 24 hours before exposure to the ionizing radiation.

64. The method of claim 63 wherein the radioprotective compound is administered about 18 hours and about 6 hours before exposure to the ionizing radiation.

65. The method of claim 60, wherein the radioprotective compound is administered after exposure to ionizing radiation.

66. The method of claim 65, wherein the radioprotective compound is administered between 0–6 hours after exposure to ionizing radiation.

67. A method of treating a subject a proliferative disorder, comprising:
(a) administering to the subject an effective amount of at least one radioprotective compound of the formula:

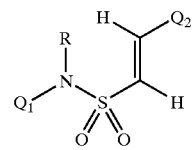

wherein:
$Q_1$ and $Q_2$ are independently selected from the group consisting of substituted and unsubstituted aryl, and substituted and unsubstituted heteroaryl;
R is selected from the group consisting of hydrogen, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$ hydroxyalkyl, substituted aryl, unsubstituted aryl, substituted heteroaryl, unsubstituted heteroaryl, substituted aryl$(C_1-C_3)$alkyl, unsubstituted aryl$(C_1-C_3)$ alkyl, substituted heteroaryl$(C_1-C_3)$alkyl and unsubstituted heteroaryl$(C_1-C_3)$alkyl;
wherein the substituents for the substituted aryl and substituted heteroaryl groups comprising $Q_1$ are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$ hydroxyalkyl, phosphonato, amino, $(C_1-C_6)$acylamino, sulfamyl, acetoxy, di$(C_1-C_6)$alkylamino$(C_2-C_6)$ alkoxy, trifluoromethyl and

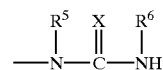

wherein:
X is oxygen or sulfur,
$R^5$ is selected from the group consisting of hydrogen, $(C_1-C_6)$alkyl, $(C_2-C_6)$heteroalkyl, substituted phenyl and unsubstituted phenyl, and $R^6$ is selected from the group consisting of hydrogen, $(C_1-C_6)$alkyl, $(C_2-C_6)$heteroalkyl, substituted aryl, unsubstituted aryl, substituted heteroaryl, unsubstituted heteroaryl, substituted aryl$(C_1-C_3)$alkyl, unsubstituted aryl-$(C_1-C_3)$alkyl and $(C_1-C_6)$ alkoxycarbonyl$(C_1-C_6)$alkylenyl;

wherein the substituents for the substituted aryl and substituted heteroaryl groups comprising $Q_2$, and the substituents for the substituted aryl and substituted heteroaryl groups comprising or included within R, $R^5$ and $R^6$, are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$ acylamino, sulfamyl, acetoxy, di$(C_1-C_6)$alkylamino $(C_2-C_6)$alkoxy and trifluoromethyl;

or a pharmaceutically acceptable salt thereof; and (b) administering an effective amount of therapeutic ionizing radiation.

68. The method of claim 67 wherein the proliferative disorder is cancer.

69. A method for treating a subject who has incurred or is at risk for incurring remediable radiation damage from exposure to ionizing radiation, comprising administering an effective amount of at least one radioprotective compound of the following formula prior to or after incurring remedial radiation damage from exposure to ionizing radiation:

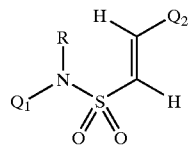

I wherein:

$Q_1$ and $Q_2$ are independently selected from the group consisting of substituted and unsubstituted aryl, and substituted and unsubstituted heteroaryl;

R is selected from the group consisting of hydrogen, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$ hydroxyalkyl, substituted aryl, unsubstituted aryl, substituted heteroaryl, unsubstituted heteroaryl, substituted aryl$(C_1-C_3)$alkyl, unsubstituted aryl$(C_1-C_3)$ alkyl, substituted heteroaryl$(C_1-C_3)$alkyl and unsubstituted heteroaryl$(C_1-C_3)$alkyl;

wherein the substituents for the substituted aryl and substituted heteroaryl groups comprising $Q_1$ are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$ hydroxyalkyl, phosphonato, amino, $(C_1-C_6)$acylamino, sulfamyl, acetoxy, di$(C_1-C_6)$alkylamino$(C_2-C_6)$ alkoxy, trifluoromethyl and

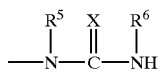

wherein:

X is oxygen or sulfur, $R^5$ is selected from the group consisting of hydrogen, $(C_1-C_6)$alkyl, $(C_2-C_6)$heteroalkyl, substituted phenyl and unsubstituted phenyl, and $R^6$ is selected from the group consisting of hydrogen, $(C_1-C_6)$alkyl, $(C_2-C_6)$heteroalkyl, substituted aryl, unsubstituted aryl, substituted heteroaryl, unsubstituted heteroaryl, substituted aryl$(C_1-C_3)$alkyl, unsubstituted aryl-$(C_1-C_3)$alkyl and $(C_1-C_6)$ alkoxycarbonyl$(C_1-C_6)$alkylenyl;

wherein the substituents for the substituted aryl and substituted heteroaryl groups comprising $Q_2$, and the substituents for the substituted aryl and substituted heteroaryl groups comprising or included within R, $R^5$ and $R^6$, are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$ acylamino, sulfamyl, acetoxy, di$(C_1-C_6)$alkylamino $(C_2-C_6$ alkoxy) and trifluoromethyl;

or a pharmaceutically acceptable salt thereof.

70. A process for preparing a compound according to claim 1, comprising reacting a compound of the formula $Q_2$—CH=CH—SO$_2$Cl with a compound of the formula $Q_1$—NRH in a nonprotic solvent in the presence of a base to form a compound formula:

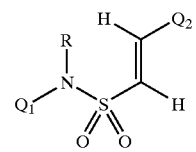

I wherein:

$Q_1$ and $Q_2$ are independently selected from the group consisting of substituted and unsubstituted aryl, and substituted and unsubstituted heteroaryl;

R is selected from the group consisting of hydrogen, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$ hydroxyalkyl, substituted aryl, unsubstituted aryl, substituted heteroaryl, unsubstituted heteroaryl, substituted aryl$(C_1-C_3)$alkyl, unsubstituted aryl$(C_1-C_3)$ alkyl, substituted heteroaryl$(C_1-C_3)$alkyl and unsubstituted heteroaryl$(C_1-C_3)$alkyl;

wherein the substituents for the substituted aryl and substituted heteroaryl groups comprising $Q_1$ are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$ hydroxyalkyl, phosphonato, amino, $(C_1-C_6)$acylamino, sulfamyl, acetoxy, di$(C_1-C_6)$alkylamino$(C_2-C_6)$ alkoxy, trifluoromethyl and

wherein:

X is oxygen or sulfur, $R^5$ is selected from the group consisting of hydrogen, $(C_1-C_6)$alkyl, $(C_2-C_6)$heteroalkyl, substituted phenyl and unsubstituted phenyl, and $R^6$ is selected from the group consisting of hydrogen, $(C_1-C_6)$alkyl, $(C_2-C_6)$heteroalkyl, substituted aryl, unsubstituted aryl, substituted heteroaryl, unsubstituted heteroaryl, substituted aryl-$(C_1-C_3)$alkyl, unsubstituted aryl-$(C_1-C_3)$alkyl and $(C_1-C_6)$ alkoxycarbonyl$(C_1-C_6)$alkylenyl; and wherein the substituents for the substituted aryl and substituted heteroaryl groups comprising $Q_2$, and the substituents for the substituted aryl and substituted heteroaryl groups comprising or included within R, $R^5$ and $R^6$, are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$ acylamino, sulfamyl, acetoxy, di$(C_1-C_6)$alkylamino $(C_2-C_6)$alkoxy and trifluoromethyl;

provided, that when R is hydrogen:

(a) when $Q_1$ is unsubstituted phenyl, $Q_2$ is other than dimethoxyphenyl, 2-methylphenyl, 2-chlorophenyl, 4-chlorophenyl, 4-N,N-dimethylaminophenyl, 4-methylphenyl, 4-methoxyphenyl, 4-nitrophenyl, 3-methoxy-4-hydroxyphenyl, unsubstituted phenyl, unsubstituted phenyl, unsubstituted benzodioxolyl, unsubstituted 1-naphthyl and unsubstituted 2-thienyl;

(b) when $Q_1$ is 2,4-dinitrophenyl, $Q_2$ is other than 4-methylphenyl, 4-methoxyphenyl, 4-nitrophenyl, 4-bromophenyl, 3,4-dichlorophenyl, unsubstituted phenyl or unsubstituted 1-naphthyl; in a sub-embodiment, when $Q_1$ is 2,4-dinitrophenyl, $Q_2$ is other than 4-alkylphenyl, 4-alkoxyphenyl, 4-nitrophenyl, 4-halophenyl, 3,4-dihalophenyl, unsubstituted phenyl or unsubstituted 1-naphthyl;

(c) when $Q_1$ is 3-hydroxyphenyl, $Q_2$ is other than 2-nitrophenyl, or 3-nitrophenyl;

(d) when $Q_1$ is 2-methyl-5-hydroxyphenyl, $Q_2$ is other than 4-nitrophenyl;

(e) when $Q_1$ is unsubstituted 2-pyridyl, Q2 is other than 3-methoxy-4-hydroxyphenyl; and (f) when $Q_2$ is unsubstituted phenyl, $Q_1$ is other than 2-hydroxyphenyl, 2-aminophenyl, 3,4-dichlorophenyl or unsubstituted 2-pyridyl;

or a pharmaceutically acceptable salt thereof.

71. A process according to claim 70, provided:

(a) when $Q_1$ is unsubstituted phenyl, $Q_2$ is other than dialkoxyphenyl, 2-alkylphenyl, 2-halophenyl, 4-halophenyl, 4-N,N-dialkylaminophenyl, 4-alkylphenyl, 4-alkoxyphenyl, 4-nitrophenyl, 3-alkoxy-4-hydroxyphenyl, unsubstituted phenyl, unsubstituted pyrenyl, unsubstituted benzodioxolyl, unsubstituted 1-naphthyl and unsubstituted 2-thienyl;

(b) when $Q_1$ is 2,4-dinitrophenyl, $Q_2$ is other than 4-alkylphenyl, 4-alkoxyphenyl, 4-nitrophenyl, 4-halophenyl, 3,4-dihalophenyl, unsubstituted phenyl or unsubstituted 1-naphthyl;

(c) when $Q_1$ is 3-hydroxyphenyl, $Q_2$ is other than nitrophenyl;

(d) when $Q_1$ is 2-methyl-5-hydroxyphenyl, $Q_2$ is other than 4-nitrophenyl;

(e) when $Q_1$ is unsubstituted 2-pyridyl, $Q_2$ is other than 3-methoxy-4-hydroxyphenyl; and (f) when $Q_2$ is unsubstituted phenyl, $Q_1$ is other than 2-hydroxyphenyl, 2-aminophenyl, 3,4-dihalophenyl or unsubstituted 2-pyridyl;

or a pharmaceutically acceptable salt thereof.

72. A process for preparing a compound according to claim 1, comprising reacting a compound of the formula

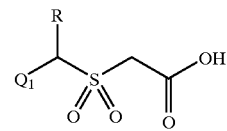

with a compound of the formula $Q_2$—C(O)H in a nonprotic solvent in the presence of a base to form a compound formula:

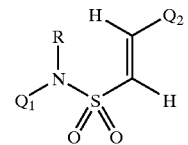

wherein:

$Q_1$ and $Q_2$ are independently selected from the group consisting of substituted and unsubstituted aryl, and substituted and unsubstituted heteroaryl;

R is selected from the group consisting of hydrogen, $(C_1-C_6)$alkyl, $(C_1-C_6)$alkoxy, $(C_3-C_6)$alkenyl, $(C_2-C_6)$heteroalkyl, $(C_3-C_6)$heteroalkenyl, $(C_2-C_6)$ hydroxyalkyl, substituted aryl, unsubstituted aryl, substituted heteroaryl, unsubstituted heteroaryl, substituted aryl$(C_1-C_3)$alkyl, unsubstituted aryl$(C_1-C_3)$ alkyl, substituted heteroaryl$(C_1-C_3)$alkyl and unsubstituted heteroaryl$(C_1-C_3)$alkyl;

wherein the substituents for the substituted aryl and substituted heteroaryl groups comprising $Q_1$ are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$ hydroxyalkyl, phosphonato, amino, $(C_1-C_6)$acylamino, sulfamyl, acetoxy, di$(C_1-C_6)$alkylamino$(C_2-C_6)$ alkoxy, trifluoromethyl and

wherein:

X is oxygen or sulfur, $R^5$ is selected from the group consisting of hydrogen, $(C_1-C_6)$alkyl, $(C_2-C_6)$heteroalkyl, substituted phenyl and unsubstituted phenyl, and $R^6$ is selected from the group consisting of hydrogen, $(C_1-C_6)$alkyl, $(C_2-C_6)$heteroalkyl, substituted aryl, unsubstituted aryl, substituted heteroaryl, unsubstituted heteroaryl, substituted aryl-$(C_1-C_3)$alkyl, unsubstituted aryl-$(C_1-C_3)$alkyl and $(C_1-C_6)$ alkoxycarbonyl$(C_1-C_6)$alkylenyl; and wherein the substituents for the substituted aryl and substituted heteroaryl groups comprising $Q_2$, and the substituents for the substituted aryl and substituted heteroaryl groups comprising or included within R, $R^5$ and $R^6$, are independently selected from the group consisting of halogen, $(C_1-C_6)$alkyl, $(C_1-C_6)$alkoxy, nitro, cyano, carboxy, carboxy$(C_1-C_3)$alkoxy, hydroxy, $(C_2-C_6)$hydroxyalkyl, phosphonato, amino, $(C_1-C_6)$ acylamino, sulfamyl, acetoxy, di$(C_1-C_6)$alkylamino $(C_2-C_6)$alkoxy and trifluoromethyl;

provided, that when R is hydrogen:
  (a) when $Q_1$ is unsubstituted phenyl, $Q_2$ is other than dimethoxyphenyl, 2-methylphenyl, 2-chlorophenyl, 4-chlorophenyl, 4-N-dimethylphenyl, 4-methylphenyl, 4-methoxyphenyl, 4-nitrophenyl, 3-methoxy-4-hydroxyphenyl, unsubstituted phenyl, unsubstituted phenyl, unsubstituted benzodioxolyl, unsubstituted 1-naphthyl and unsubstituted 2-thienyl;
  (b) when $Q_1$ is 2,4-dinitrophenyl, $Q_2$ is other than 4-methylphenyl, 4-methoxyphenyl, 4-nitrophenyl, 4-bromophenyl, 3,4-dichlorophenyl, unsubstituted phenyl or unsubstituted 1-naphthyl;
  (c) when $Q_1$ is 3-hydroxyphenyl, $Q_2$ is other than 2-nitrophenyl, or 3-nitrophenyl; in a sub-embodiment, when $Q_1$ is 3-hydroxyphenyl, $Q_2$ is other than nitrophenyl;
  (d) when $Q_1$ is 2-methyl-5-hydroxyphenyl, $Q_2$ is other than 4-nitrophenyl;
  (e) when $Q_1$ is unsubstituted 2-pyridyl, $Q_2$ is other than 3-methoxy-4-hydroxyphenyl; and
  (f) when $Q_2$ is unsubstituted phenyl, $Q_1$ is other than 2-hydroxyphenyl, 2-aminophenyl, 3,4-dichlorophenyl or unsubstituted 2-pyridyl;
or a pharmaceutically acceptable salt thereof.

73. A process for preparing a compound according to claim 72, provided:
  (a) when $Q_1$ is unsubstituted phenyl, $Q_2$ is other than dialkoxyphenyl, 2-alkylphenyl, 2-halophenyl, 4-halophenyl, 4-N,N-dialkylaminophenyl, 4-alkylphenyl, 4-alkoxyphenyl, 4-nitrophenyl, 3-alkoxy-4-hydroxyphenyl, unsubstituted phenyl, unsubstituted pyrenyl, unsubstituted benzodioxolyl, unsubstituted 1-naphthyl and unsubstituted 2-thienyl;
  (b) when $Q_1$ is 2,4-dinitrophenyl, $Q_2$ is other than 4-alkylphenyl, 4-alkoxyphenyl, 4-nitrophenyl, 4-halophenyl, 3,4-dihalophenyl, unsubstituted phenyl or unsubstituted 1-naphthyl;
  (c) when $Q_1$ is 3-hydroxyphenyl, $Q_2$ is other than nitrophenyl;
  (d) when $Q_1$ is 2-methyl-5-hydroxyphenyl, $Q_2$ is other than 4-nitrophenyl;
  (e) when $Q_1$ is unsubstituted 2-pyridyl, $Q_2$ is other than 3-methoxy-4-hydroxyphenyl; and
  (f) when $Q_2$ is unsubstituted phenyl, $Q_1$ is other than 2-hydroxyphenyl, 2-aminophenyl, 3,4-dihalophenyl or unsubstituted 2-pyridyl;
or a pharmaceutically acceptable salt thereof.

74. A method of reducing the number of malignant cells in bone marrow of a subject, comprising:
  (1) removing a portion of the subject's bone marrow;
  (2) administering an effective amount of at least one radioprotective N-aryl-2-arylethenesulfonamide to the bone marrow;
  (3) irradiating the bone marrow with an effective amount of ionizing radiation.

75. The method of claim 74, further comprising reimplanting the bone marrow into the subject.

76. The method of claim 74, wherein the subject receives therapeutic ionizing radiation prior to reimplantation of the bone marrow, and is administered at least one radioprotective N-aryl-2-arylethenesulfonamide prior to receiving the therapeutic ionizing radiation.

77. The method of claim 74 wherein the radioprotective compound is administered at least about 6 hours before exposure of the bone marrow to the ionizing radiation.

78. The method of to claim 74 wherein the radioprotective compound is administered about 20 hours before exposure to the ionizing radiation.

79. The method of claim 74 wherein the radioprotective compound is administered about 24 hours before exposure to the ionizing radiation.

* * * * *

UNITED STATES PATENT AND TRADEMARK OFFICE
CERTIFICATE OF CORRECTION

PATENT NO.   : 6,646,009 B2  
DATED        : November 11, 2003  
INVENTOR(S)  : Reddy et al.

It is certified that error appears in the above-identified patent and that said Letters Patent is hereby corrected as shown below:

Column 52,
Line 1, replace the structure:

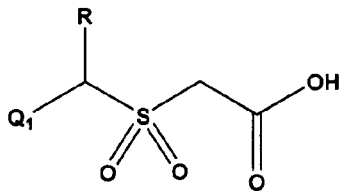

with the structure

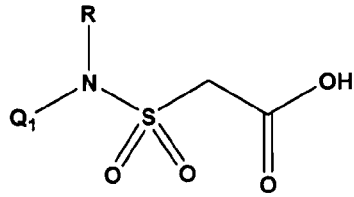

UNITED STATES PATENT AND TRADEMARK OFFICE
CERTIFICATE OF CORRECTION

PATENT NO.    : 6,646,009 B2
DATED         : November 11, 2003
INVENTOR(S)   : Reddy et al.

It is certified that error appears in the above-identified patent and that said Letters Patent is hereby corrected as shown below:

Column 18,
Lines 20-30, replace the structure of Formula I:

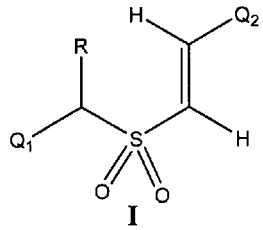

with the structure

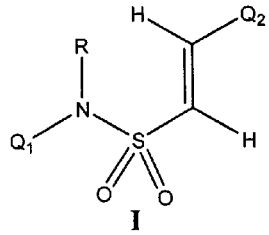

Signed and Sealed this

Thirty-first Day of August, 2004

JON W. DUDAS
*Director of the United States Patent and Trademark Office*